United States Patent [19]

Schallner et al.

[11] Patent Number: 5,039,334

[45] Date of Patent: Aug. 13, 1991

[54] HERBICIDAL AND PLANT GROWTH-REGULATING SUBSTITUTED N-ARYL NITROGEN HETEROCYCLES

[75] Inventors: Otto Schallner; Reiner Fischer, both of Monheim; Albrecht Marhold, Leverkusen; Karl-Julius Reubke, Cologne; Hans-Joachim Santel, Leverkusen; Robert R. Schmidt; Klaus Lürssen, both of Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 354,328

[22] Filed: May 19, 1989

[30] Foreign Application Priority Data

Jun. 8, 1988 [DE] Fed. Rep. of Germany ....... 3819439

[51] Int. Cl.[5] .................. A01N 43/36; C07D 209/44; C07D 207/444

[52] U.S. Cl. .......................................... 71/95; 71/94; 71/96; 546/121; 548/513; 548/515; 548/549

[58] Field of Search ....................... 548/513, 515, 549; 546/121; 71/94, 95, 96

[56] References Cited

U.S. PATENT DOCUMENTS

| | | | |
|---|---|---|---|
| 3,654,302 | 4/1972 | Schwatz et al. ........................ | 21/96 |
| 4,124,375 | 11/1978 | Bollinger et al. ....................... | 71/96 |
| 4,484,940 | 11/1984 | Nagano et al. ......................... | 71/96 |

FOREIGN PATENT DOCUMENTS

| | | | |
|---|---|---|---|
| 49511 | 4/1982 | European Pat. Off. ............ | 548/513 |
| 0068822 | 1/1983 | European Pat. Off. . | |
| 0190755 | 8/1986 | European Pat. Off. . | |
| 0215424 | 3/1987 | European Pat. Off. . | |
| 0234323 | 9/1987 | European Pat. Off. . | |
| 0259264 | 3/1988 | European Pat. Off. . | |
| 0259265 | 3/1988 | European Pat. Off. . | |
| 0260228 | 3/1988 | European Pat. Off. . | |
| 288960 | 11/1988 | European Pat. Off. ............ | 548/513 |
| 57-62256 | 4/1982 | Japan .................................. | 548/513 |
| 280471 | 12/1986 | Japan .................................. | 548/513 |

*Primary Examiner*—C. Warren Ivy

*Assistant Examiner*—Celia Chang

*Attorney, Agent, or Firm*—Sprung Horn Kramer & Woods

[57] ABSTRACT

Herbicidal and plant growth-regulating substituted N-aryl nitrogen heterocycles of the formula (I)

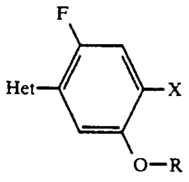

in which

Het stands for

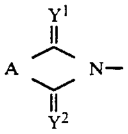

or

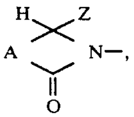

where

A stands for

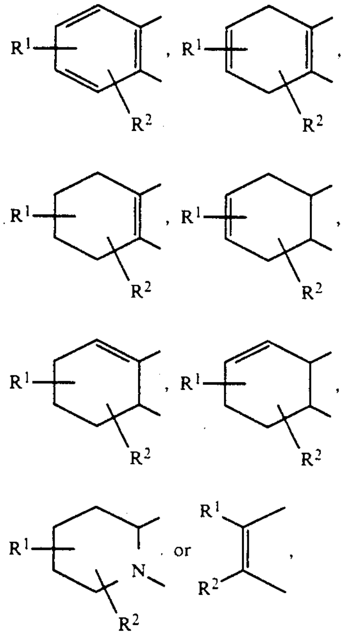

where $R^1$ and $R^2$ in each case independently of one another stand for hydrogen, halogen, halogenoalkyl or alkyl, $Y^1$ and $Y^2$ in each case stand for oxygen or sulphur and Z stands for hydrogen, hydroxyl or chlorine, R stands for alkyl, alkenyl, cycloalkyl, cycloalkenyl, cycloalylalkyl, or cycloalkenylalkyl, in each case optionally branched and in each case interrupted by at least one oxygen atom, and X stands for hydrogen or halogen.

Intermediates of the formula (III)

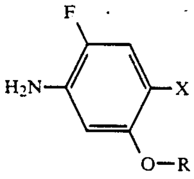

are also new.

17 Claims, No Drawings

HERBICIDAL AND PLANT GROWTH-REGULATING SUBSTITUTED N-ARYL NITROGEN HETEROCYCLES

The present invention relates to novel substituted N-aryl nitrogen heterocycles, processes for their preparation and their use as herbicides and as plant growth regulators.

It is known that certain nitrogen heterocycles, such as, for example, 5-tert-butyl-3-(2,4-dichloro-5-isopropoxy-phenyl)-1,3,4-oxadiazol-2-one (oxadiazone/-®Ronstar) exhibit herbicidal properties (cf. U.S. Pat. No. 3,835,862).

However, the action of these compounds is not satisfactory at low application rates or active compound concentrations.

The novel substituted N-aryl nitrogen heterocycles of the general formula (I)

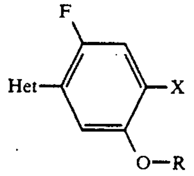
(I)

in which

Het stands for one of the heterocyclic groups below

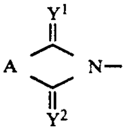 or 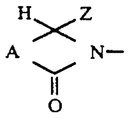

where

A stands for one of the groups below

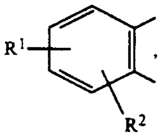 , 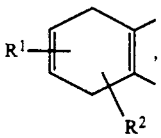 , 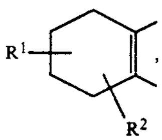 ,

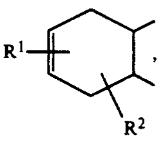 , 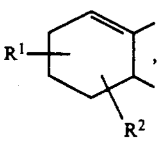 , 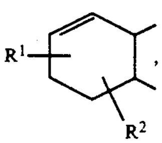 ,

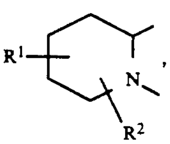 , 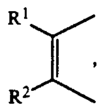 , where $R^1$ and $R^2$ in each case independently of one another stand for hydrogen, halogen, halogenoalkyl or alkyl, $Y^1$ and $Y^2$ in each case stand for oxygen or sulphur and Z stands for hydrogen, hydroxyl or chlorine, R stands for alkyl, alkenyl, cycloalkyl, cycloalkenyl, cycloalkylalkyl or cycloalkenylalkyl, in each case optionally branched and in each case interrupted by at least one oxygen atom, and X stands for hydrogen or halogen, have now been found.

Furthermore, it has been found that the novel substituted N-aryl nitrogen heterocycles of the general formula (I) are obtained when (a) in the event that Het stands for the group

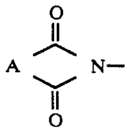

and

A, R and X have the abovementioned meanings, cyclic anhydrides of the general formula (II)

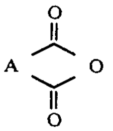

in which

A has the abovementioned meaning, are reacted with arylamines of the general formula (III)

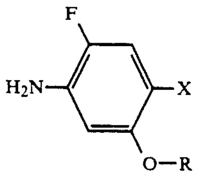
(III)

in which

R and X have the abovementioned meanings, if appropriate in the presence of a diluent and if appropriate in the presence of a reaction auxiliary, or when (b) in the event that Het stands for the group

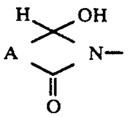

and

A, R and X have the abovementioned meanings, substituted arylimides of the general formula (Ia)

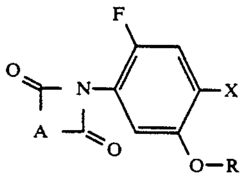
(Ia)

in which

A, R and X have the abovementioned meanings, are reacted with a reducing agent, if appropriate in the presence of a diluent, or when (c) in the event that Het stands for the group

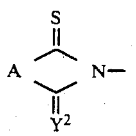

and

A, R, X and $Y^2$ have the abovementioned meanings, substituted arylimides of the general formula (Ia)

(Ia)

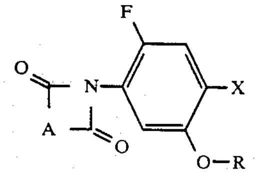

A, R and x have the abovementioned meanings, are reacted with a sulphurizing agent, if appropriate in the presence of a diluent, or when (d) in the event that Het stands for the group

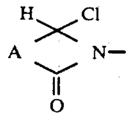

and

A, R and X have the abovementioned meanings, N-aryl nitrogen heterocycles of the general formula (Ib)

(Ib)

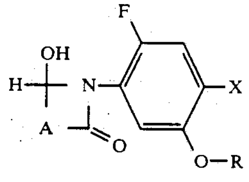

in which

A, R and X have the abovementioned meanings, are reacted with thionyl chloride, if appropriate in the presence of a diluent and if appropriate in the presence of a reaction auxiliary, or when (e) in the event that Het stands for the group

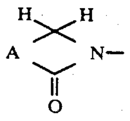

and

A, R and X have the abovementioned meanings, N-aryl nitrogen heterocycles of the general formula (Ic)

(Ic)

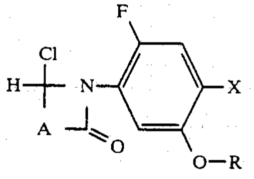

in which

A, R and X have the abovementioned meanings, are reacted with hydrogen, in the presence of a catalyst and also if appropriate in the presence of a diluent and if appropriate in the presence of an acid-binding agent, or when (f) in the event that Het stands for the group

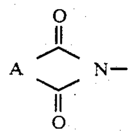

and

A, R and X have the abovementioned meanings, hydroxyarylimides of the general formula (IV)

(IV)

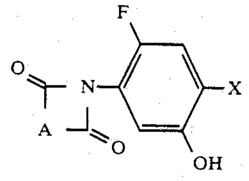

in which

A and X have the abovementioned meanings, are reacted with alkylating agents of the general formula (V)

$X^1$—R (V)

in which

R has the abovementioned meaning and $X^1$ stands for a nucleophilic leaving group, if appropriate in the presence of an acid acceptor and if appropriate in the presence of a diluent, or when (g) in the event that Het stands for the group

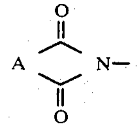

and

A and R have the abovementioned meanings and also X stands for halogen, substituted arylimides of the general formula (Id)

(Id)

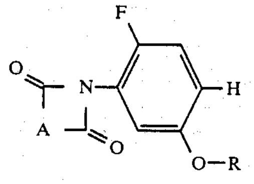

in which

A and R have the abovementioned meanings, are reacted with a halogenating agent, if appropriate in the presence of a catalyst and if appropriate in the presence of a diluent, or when (h) in the event that Het stands for the group

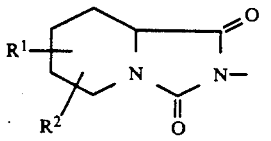

and

R, $R^1$, $R^2$ and X have the abovementioned meanings, arylamines of the general formula (III)

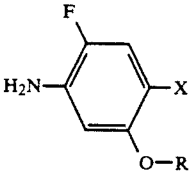

(III)

in which

R and X have the abovementioned meanings are reacted with chloroformic acid esters of the general formula (VI)

$R^3—CO—Cl$ (VI)

in which $R^3$ stands for lower alkyl, benzyl or phenyl, if appropriate in the presence of an acid acceptor and if appropriate in the presence of a diluent, and the resulting arylurethanes of the general formula (VII)

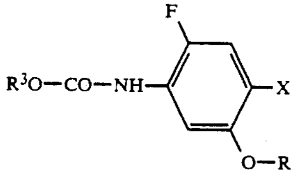

(VII)

in which

R, $R^3$ and X have the abovementioned meanings, are reacted with piperidine-2-carboxylic acid esters of the general formula (VIII)

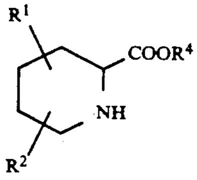

(VIII)

in which $R^1$ and $R^2$ have the abovementioned meanings and $R^4$ stands for lower alkyl, if appropriate in the presence of a diluent.

Finally, it has been found that the novel substituted N-aryl nitrogen heterocycles of the general formula (I) exhibit herbicidal and plant growth-regulating properties.

Surprisingly, the substituted N-aryl nitrogen heterocycles of the formula (I) according to the invention have a considerably more powerful action against weeds than 5-tert-butyl-3-(2,4-dichloro-5-isopropoxyphenyl)-1,3,4-oxadiazol-2-one, which is a previously known active compound of similar structure and of the same type of The invention preferably relates to compounds of the formula (I) in which Het stands for one of the heterocyclic groups below

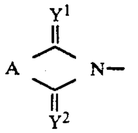 or 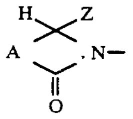

where

A stands for one of the groups below

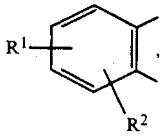, 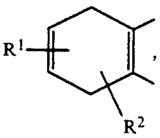, 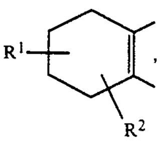,

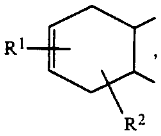, 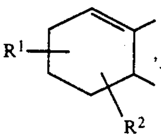, 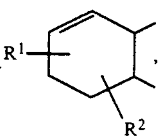,

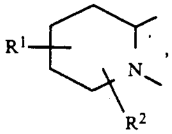, 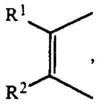, where $R^1$ and $R^2$ in each case independently of one another stand for hydrogen, fluorine, chlorine, bromine or for in each case straight-chain or branched alkyl or halogenoalkyl, in each case having 1 to 3 carbon atoms and, in the case of halogenoalkyl, having 1 to 5 identical or different halogen atoms, in particular fluorine or chlorine, $Y^1$ and $Y^2$ stand for oxygen or sulphur, Z stands for hydrogen, hydroxyl or chlorine, R stands for alkyl, alkenyl, cycloalkyl, cycloalkenyl, cycloalkylalkyl, or cycloalkenylalkyl, in each case having up to 20 carbon atoms, in each case optionally branched and in each case interrupted by 1 to 4 oxygen atoms, and X stands for hydrogen, fluorine, chlorine or bromine.

The invention particularly relates to compounds of the formula (1) in which

Het stands for one of the heterocyclic groups below

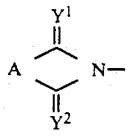 or 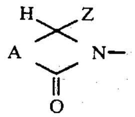

where

A stands for one of the groups below

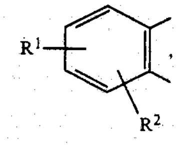, 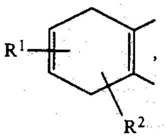, 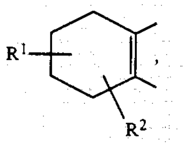,

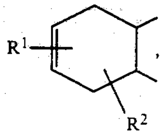, 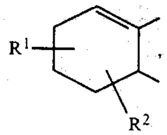, 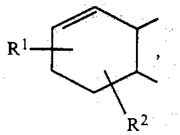,

-continued

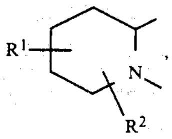, 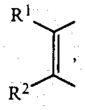, wherein $R^1$ and $R^2$ in each case independently of one another stand for hydrogen, methyl or trifluoromethyl, $Y^1$ and $Y^2$ stand for oxygen or sulphur, Z stands for hydrogen, hydroxyl or chlorine, R stands for oxaalkyl, oxaalkenyl or dioxaalkyl, in each case having up to 10 carbon atoms and in each case optionally branched, or for oxacycloalkyl-alkyl, oxacycloalkenyl-alkyl or dioxacycloalkyl-alkyl, in each case having up to 8 carbon atoms in the oxacycloalkyl, oxacycloalkenyl or dioxacrycloalkyl moiety and up to 3 carbon atoms in the alkyl moiety, and X stands for hydrogen, chlorine or bromine.

Examples for the compounds of the formula (I) according to the invention are listed in Table 1 below—cf. also the Preparation Examples.

TABLE 1

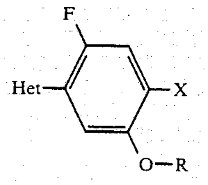 (I)

Examples of the compounds of the formula (I)

| Het | X | R |
|---|---|---|
| 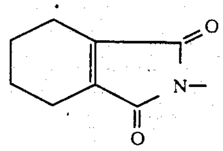 | H | $-CH_2CH_2-O-CH_2CH_2-O-CH_3$ |
| 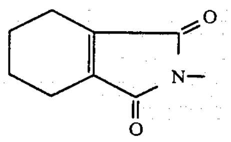 | H | $-CH_2CH_2-O-CH_2CH_2-O-C_2H_5$ |
| 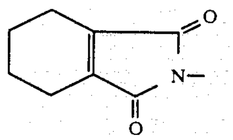 | F | $-CH_2CH_2-O-CH_2CH_2-O-CH_3$ |
| 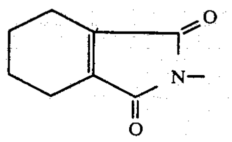 | F | $-CH_2CH_2-O-CH_2CH_2-O-C_2H_5$ |
| 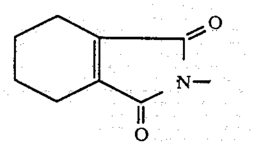 | Cl | $-CH_2CH_2-O-CH_2CH_2-O-CH_3$ |

TABLE 1-continued
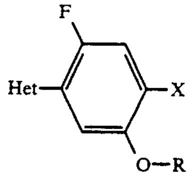
(I)
Examples of the compounds of the formula (I)
| Het | X | R |
| --- | --- | --- |
| 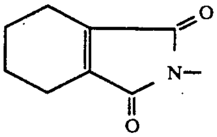 | Cl | $-CH_2CH_2-O-CH_2CH_2-O-C_2H_5$ |
| 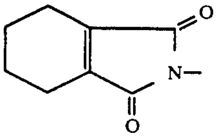 | Br | $-CH_2CH_2-O-CH_2CH_2-O-CH_3$ |
| 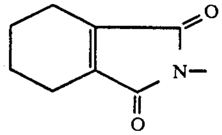 | Br | $-CH_2CH_2-O-CH_2CH_2-O-C_2H_5$ |
| 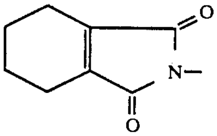 | Cl | $-CH_2CH_2-O-CH_2CH_2-O-C_3H_7$ |
| 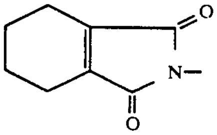 | Cl | $-CH_2CH_2-O-CH_2CH_2-O-C_4H_9$ |
| 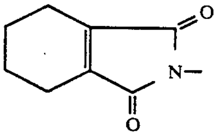 | Cl | 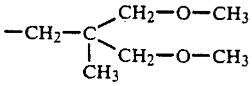 |
| 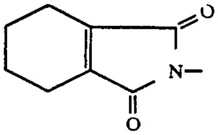 | Cl | 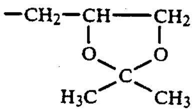 |
| 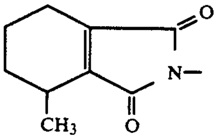 | F | $-CH_2CH_2-O-CH_2CH_2-O-CH_3$ |
| 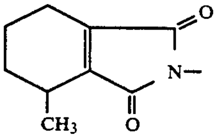 | H | $-CH_2CH_2-O-CH_2CH_2-O-C_2H_5$ |

TABLE 1-continued
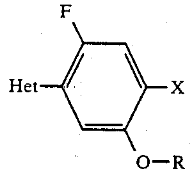
(I)
Examples of the compounds of the formula (I)
| Het | X | R |
|---|---|---|
| 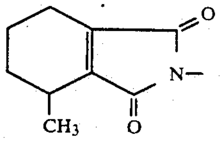 | Cl | $-CH_2CH_2-O-CH_2CH_2-O-CH_3$ |
| 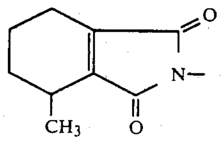 | F | $-CH_2CH_2-O-CH_2CH_2-O-C_4H_9$ |
| 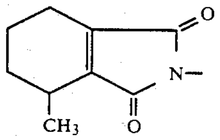 | Br | $-CH_2CH_2-O-CH_2CH_2-O-CH_3$ |
| 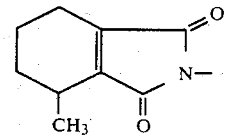 | Cl | 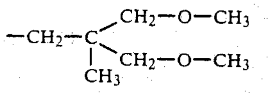 |
| 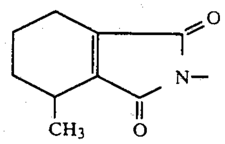 | Cl | 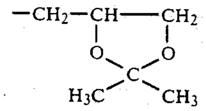 |
| 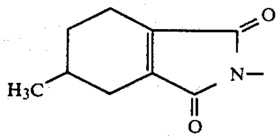 | F | $-CH_2CH_2-O-CH_2CH_2-O-CH_3$ |
| 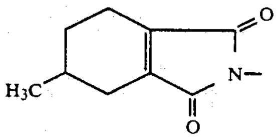 | H | $-CH_2CH_2-O-CH_2CH_2-O-C_2H_5$ |
| 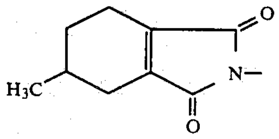 | Cl | $-CH_2CH_2-O-CH_2CH_2-O-C_2H_5$ |
| 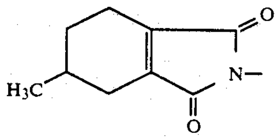 | F | $-CH_2CH_2-O-CH_2CH_2-O-C_3H_7$ |

TABLE 1-continued
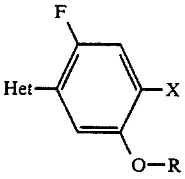
(I)
Examples of the compounds of the formula (I)
| Het | X | R |
|---|---|---|
| 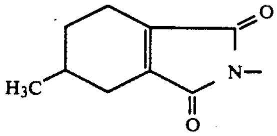 | Cl | $-CH_2CH_2-O-CH_2CH_2-O-C_4H_9$ |
| 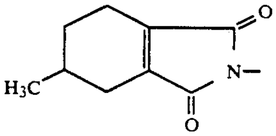 | Cl | 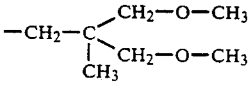 |
| 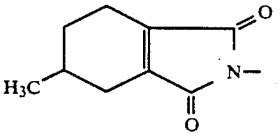 | Cl | 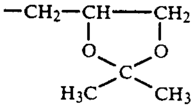 |
| 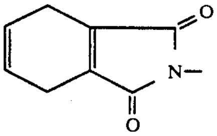 | F | $-CH_2CH_2-O-CH_2CH_2-O-CH_3$ |
| 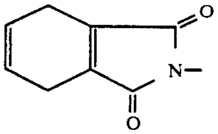 | H | $-CH_2CH_2-O-CH_2CH_2-O-CH_3$ |
| 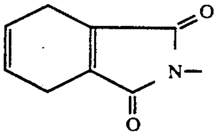 | Br | $-CH_2CH_2-O-CH_2CH_2-O-C_2H_5$ |
| 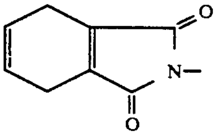 | Cl | $-CH_2CH_2-O-CH_2CH_2-O-CH_3$ |
| 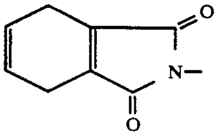 | Cl | $-CH_2CH_2-O-CH_2CH_2-O-C_2H_5$ |
| 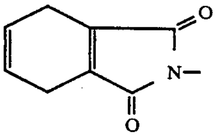 | Cl | 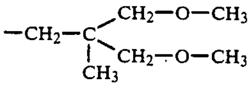 |

TABLE 1-continued
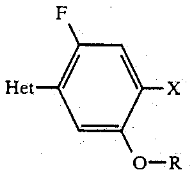
(I)
Examples of the compounds of the formula (I)
| Het | X | R |
|---|---|---|
| 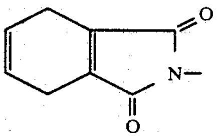 | Cl | 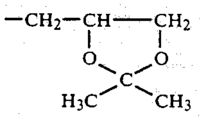 |
| 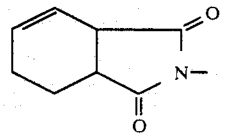 | F | $-CH_2CH_2-O-CH_2CH_2-O-CH_3$ |
| 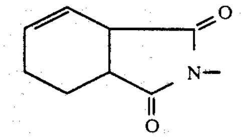 | H | $-CH_2CH_2-O-CH_2CH_2-O-C_2H_5$ |
| 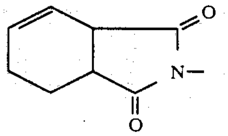 | Cl | $-CH_2CH_2-O-CH_2CH_2-O-CH_3$ |
| 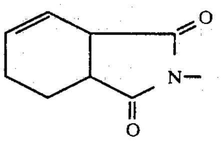 | Cl | $-CH_2CH_2-O-CH_2CH_2-O-C_2H_5$ |
| 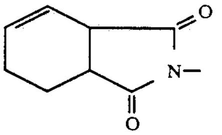 | Cl | $-CH_2CH_2-O-CH_2CH_2-O-C_4H_9$ |
| 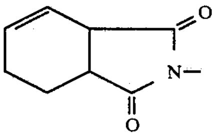 | Cl | 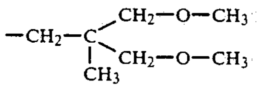 |
| 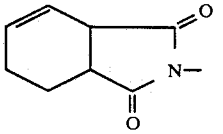 | Cl | 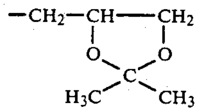 |
| 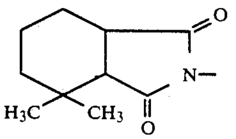 | F | $-CH_2CH_2-O-CH_2CH_2-O-CH_3$ |

TABLE 1-continued
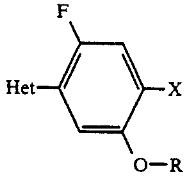
(I)
Examples of the compounds of the formula (I)
| Het | X | R |
|---|---|---|
| 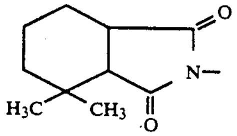 | H | $-CH_2CH_2-O-CH_2CH_2-O-C_2H_5$ |
| 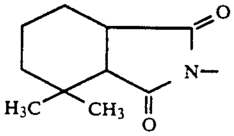 | Cl | $-CH_2CH_2-O-CH_2CH_2-O-CH_3$ |
| 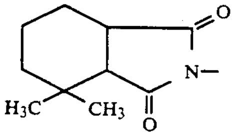 | Cl | $-CH_2CH_2-O-CH_2CH_2-O-C_2H_5$ |
| 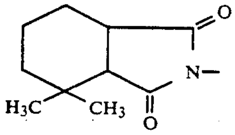 | Br | $-CH_2CH_2-O-CH_2CH_2-O-CH_3$ |
| 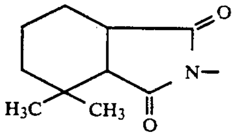 | Cl | 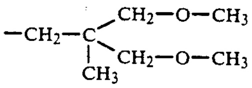 |
| 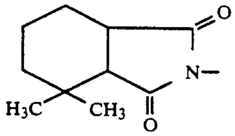 | Cl | 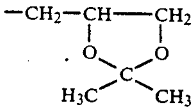 |
| 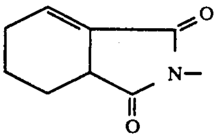 | F | $-CH_2CH_2-O-CH_2CH_2-O-CH_3$ |
| 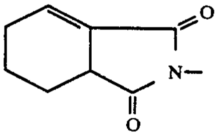 | H | $-CH_2CH_2-O-CH_2CH_2-O-C_2H_5$ |
| 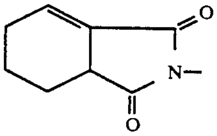 | Cl | $-CH_2CH_2-O-CH_2CH_2-O-CH_3$ |

TABLE 1-continued
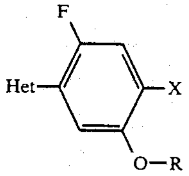
(I)
Examples of the compounds of the formula (I)
| Het | X | R |
|---|---|---|
| 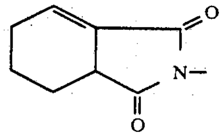 | Br | $-CH_2CH_2-O-CH_2CH_2-O-CH_3$ |
| 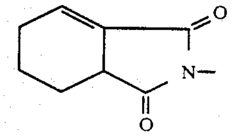 | Cl | $-CH_2CH_2-O-CH_2CH_2-O-C_2H_5$ |
| 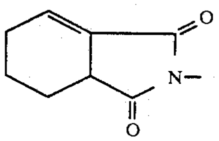 | Cl | 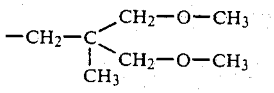 |
| 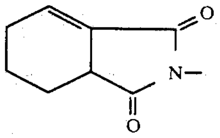 | Cl | 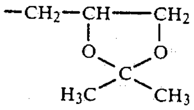 |
| 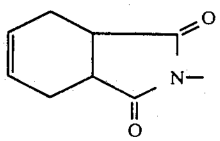 | F | $-CH_2CH_2-O-CH_2CH_2-O-CH_3$ |
| 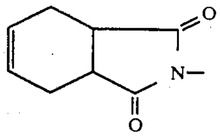 | H | $-CH_2CH_2-O-CH_2CH_2-O-C_2H_5$ |
| 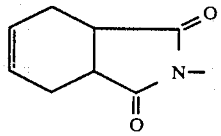 | Cl | $-CH_2CH_2-O-CH_2CH_2-O-CH_3$ |
| 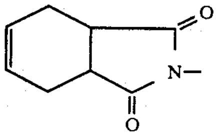 | Cl | $-CH_2CH_2-O-CH_2CH_2-O-C_2H_5$ |
| 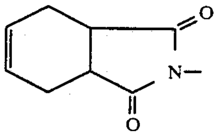 | Br | $-CH_2CH_2-O-CH_2CH_2-O-CH_3$ |

TABLE 1-continued
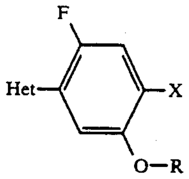
(I)
Examples of the compounds of the formula (I)
| Het | X | R |
|---|---|---|
| 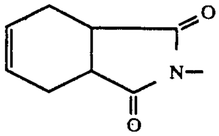 | Cl | 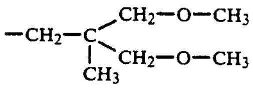 |
| 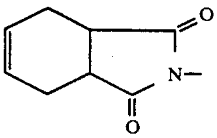 | Cl | 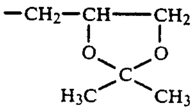 |
| 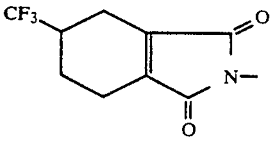 | F | $-CH_2CH_2-O-CH_2CH_2-O-CH_3$ |
| 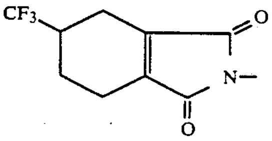 | H | $-CH_2CH_2-O-CH_2CH_2-O-C_2H_5$ |
| 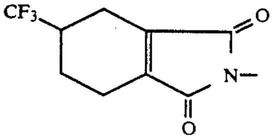 | Cl | $-CH_2CH_2-O-CH_2CH_2-O-CH_3$ |
| 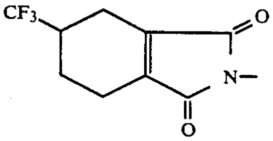 | Cl | $-CH_2CH_2-O-CH_2CH_2-O-C_2H_5$ |
| 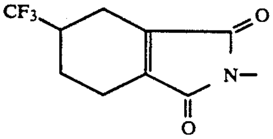 | Br | $-CH_2CH_2-O-CH_2CH_2-O-CH_3$ |
| 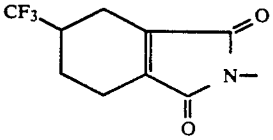 | Cl | 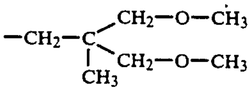 |
| 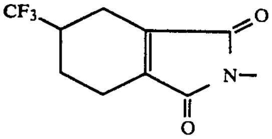 | Cl | 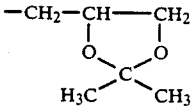 |

TABLE 1-continued
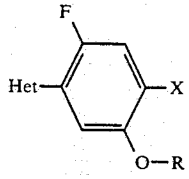
(I)
Examples of the compounds of the formula (I)
| Het | X | R |
|---|---|---|
| 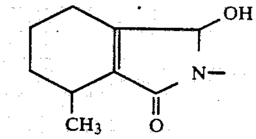 | F | $-CH_2CH_2-O-CH_2CH_2-O-CH_3$ |
| 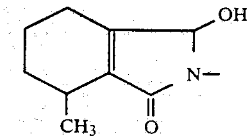 | H | $-CH_2CH_2-O-CH_2CH_2-O-C_2H_5$ |
| 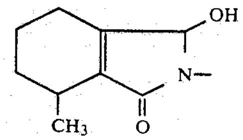 | Cl | $-CH_2CH_2-O-CH_2CH_2-O-CH_3$ |
| 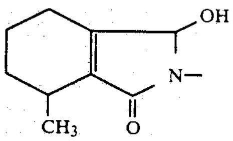 | Cl | $-CH_2CH_2-O-CH_2CH_2-O-C_2H_5$ |
| 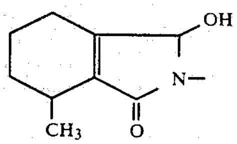 | Br | $-CH_2CH_2-O-CH_2CH_2-O-CH_3$ |
| 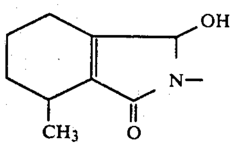 | Cl | 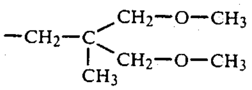 |
| 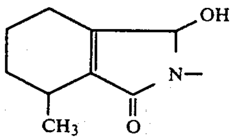 | Cl | 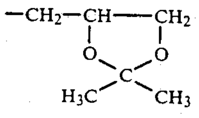 |
| 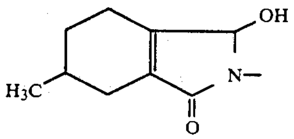 | F | $-CH_2CH_2-O-CH_2CH_2-O-CH_3$ |
| 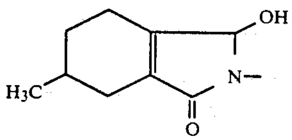 | H | $-CH_2CH_2-O-CH_2CH_2-O-C_2H_5$ |

TABLE 1-continued
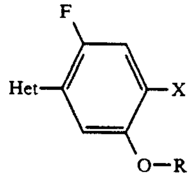
(I)
Examples of the compounds of the formula (I)
| Het | X | R |
|---|---|---|
| 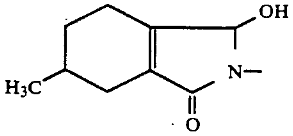 | Cl | $-CH_2CH_2-O-CH_2CH_2-O-CH_3$ |
| 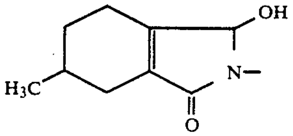 | Cl | $-CH_2CH_2-O-CH_2CH_2-O-C_2H_5$ |
| 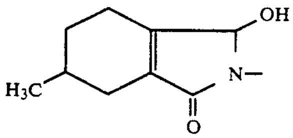 | Br | $-CH_2CH_2-O-CH_2CH_2-O-CH_3$ |
| 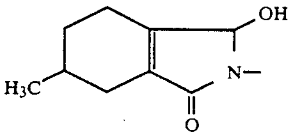 | Cl | 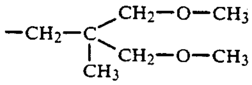 |
| 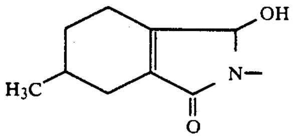 | Cl | 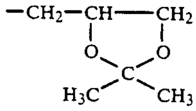 |
| 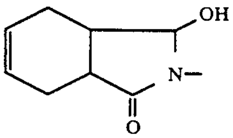 | F | $-CH_2CH_2-O-CH_2CH_2-O-CH_3$ |
| 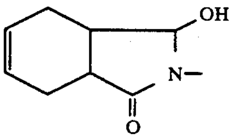 | H | $-CH_2CH_2-O-CH_2CH_2-O-C_2H_5$ |
| 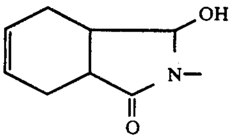 | Cl | $-CH_2CH_2-O-CH_2CH_2-O-CH_3$ |
| 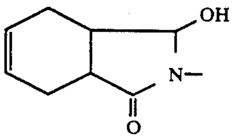 | Cl | $-CH_2CH_2-O-CH_2CH_2-O-C_2H_5$ |

TABLE 1-continued
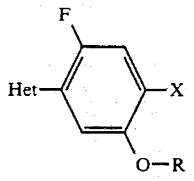
(I)
Examples of the compounds of the formula (I)
| Het | X | R |
|---|---|---|
| 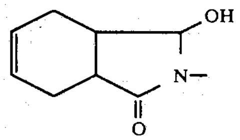 | Br | $-CH_2CH_2-O-CH_2CH_2-O-CH_3$ |
| 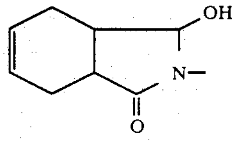 | Cl | 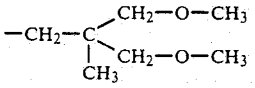 |
| 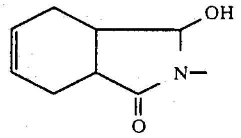 | Cl | 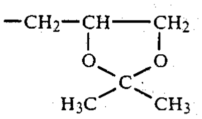 |
| 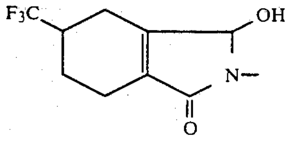 | F | $-CH_2CH_2-O-CH_2CH_2-O-CH_3$ |
| 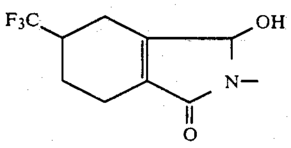 | H | $-CH_2CH_2-O-CH_2CH_2-O-C_2H_5$ |
| 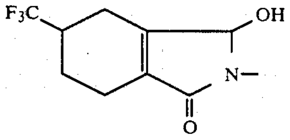 | Cl | $-CH_2CH_2-O-CH_2CH_2-O-CH_3$ |
| 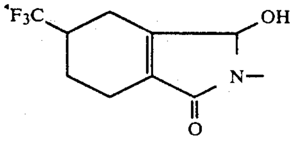 | Cl | $-CH_2CH_2-O-CH_2CH_2-O-C_2H_5$ |
| 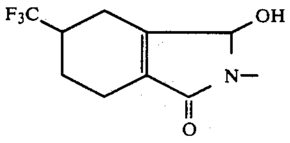 | Br | $-CH_2CH_2-O-CH_2CH_2-O-CH_3$ |
| 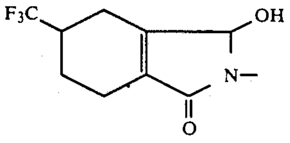 | Cl | 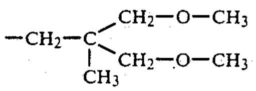 |

TABLE 1-continued
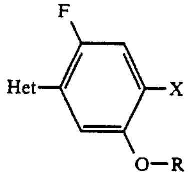
(I)
Examples of the compounds of the formula (I)
| Het | X | R |
|---|---|---|
| 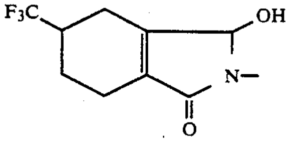 | Cl | 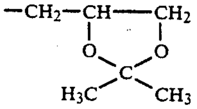 |
| 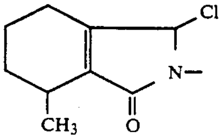 | F | $-CH_2CH_2-O-CH_2CH_2-O-C_2H_5$ |
| 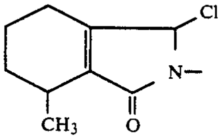 | H | $-CH_2CH_2-O-CH_2CH_2-O-CH_3$ |
| 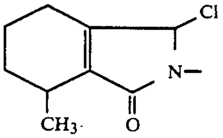 | Cl | $-CH_2CH_2-O-CH_2CH_2-O-CH_3$ |
| 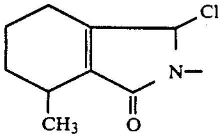 | Cl | $-CH_2CH_2-O-CH_2CH_2-O-C_2H_5$ |
| 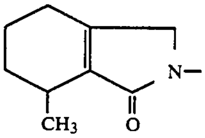 | F | $-CH_2CH_2-O-CH_2CH_2-O-C_2H_5$ |
| 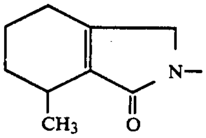 | Cl | $-CH_2CH_2-O-CH_2CH_2-C_2H_5$ |
| 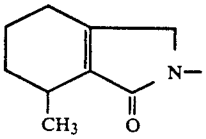 | Br | $-CH_2CH_2-O-CH_2CH_2-O-CH_3$ |
| 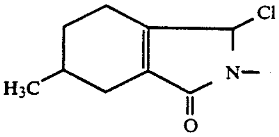 | F | $-CH_2CH_2-O-CH_2CH_2-O-C_2H_5$ |

TABLE 1-continued
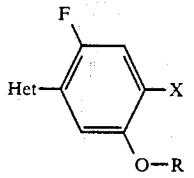
(I)
Examples of the compounds of the formula (I)
| Het | X | R |
|---|---|---|
| 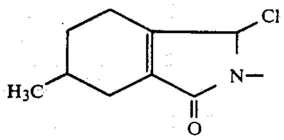 | Cl | $-CH_2CH_2-O-CH_2CH_2-O-CH_3$ |
| 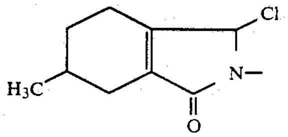 | Cl | $-CH_2CH_2-O-CH_2CH_2-O-C_2H_5$ |
| 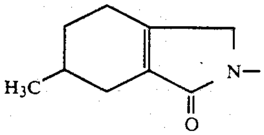 | F | $-CH_2CH_2-O-CH_2CH_2-O-C_2H_5$ |
| 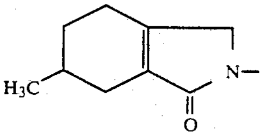 | Cl | $-CH_2CH_2-O-CH_2CH_2-O-C_2H_5$ |
| 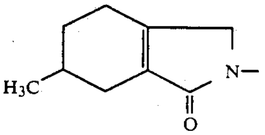 | Br | $-CH_2CH_2-O-CH_2CH_2-O-CH_3$ |
| 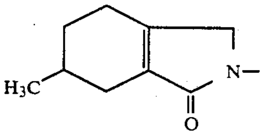 | Cl | 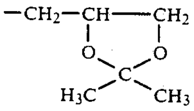 |
| 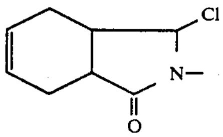 | F | $-CH_2CH_2-O-CH_2CH_2-O-C_2H_5$ |
| 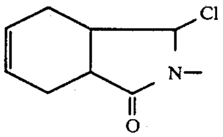 | H | $-CH_2CH_2-O-CH_2CH_2-O-C_4H_9$ |
| 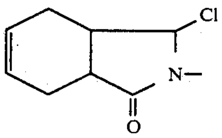 | Cl | $-CH_2CH_2-O-CH_2CH_2-O-CH_3$ |

TABLE 1-continued
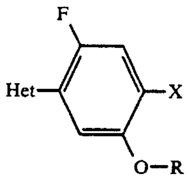
(I)
Examples of the compounds of the formula (I)
| Het | X | R |
|---|---|---|
| 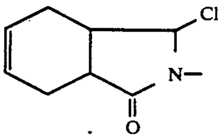 | Cl | $-CH_2CH_2-O-CH_2CH_2-O-C_2H_5$ |
| 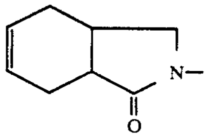 | F | $-CH_2CH_2-O-CH_2CH_2-O-C_4H_9$ |
| 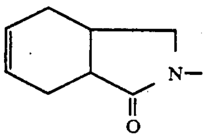 | Cl | $-CH_2CH_2-O-CH_2CH_2-O-CH_3$ |
| 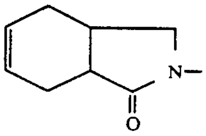 | Cl | $-CH_2CH_2-O-CH_2CH_2-O-C_2H_5$ |
| 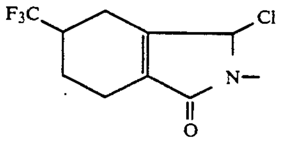 | F | $-CH_2CH_2-O-CH_2CH_2-O-C_3H_7$ |
| 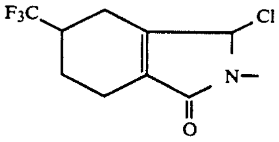 | H | $-CH_2CH_2-O-CH_2CH_2-O-C_4H_9$ |
| 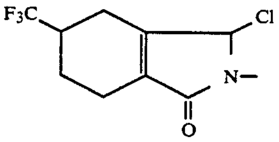 | Cl | $-CH_2CH_2-O-CH_2CH_2-O-CH_3$ |
| 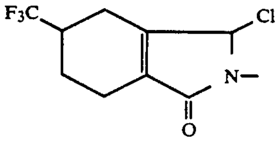 | Cl | $-CH_2CH_2-O-CH_2CH_2-O-C_2H_5$ |
| 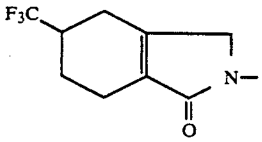 | F | $-CH_2CH_2-O-CH_2CH_2-O-C_2H_5$ |

TABLE 1-continued
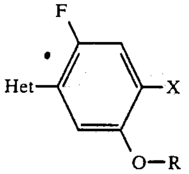
(I)
Examples of the compounds of the formula (I)
| Het | X | R |
|---|---|---|
| 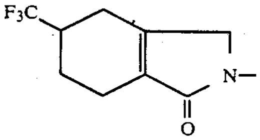 | Cl | $-CH_2CH_2-O-CH_2CH_2-O-CH_3$ |
| 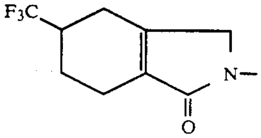 | Cl | $-CH_2CH_2-O-CH_2CH_2-O-C_2H_5$ |
| 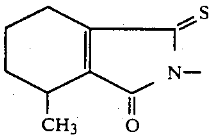 | F | $-CH_2CH_2-O-CH_2CH_2-O-CH_3$ |
| 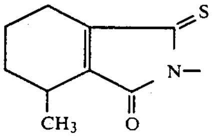 | H | $-CH_2CH_2-O-CH_2CH_2-O-CH_3$ |
| 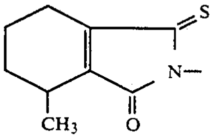 | Cl | $-CH_2CH_2-O-CH_2CH_2-O-CH_3$ |
| 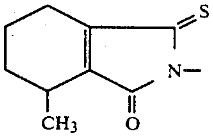 | Cl | $-CH_2CH_2-O-CH_2CH_2-O-C_2H_5$ |
| 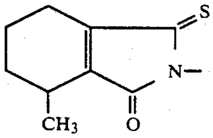 | Cl | $-CH_2CH_2-O-CH_2CH_2-O-C_3H_7$ |
| 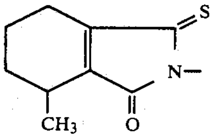 | Cl | 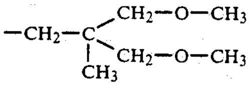 |
| 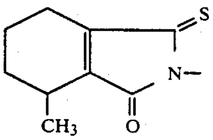 | Cl | 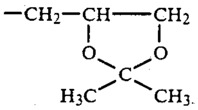 |

TABLE 1-continued
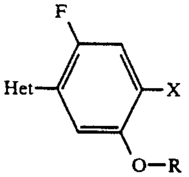
(I)
Examples of the compounds of the formula (I)
| Het | X | R |
|---|---|---|
| 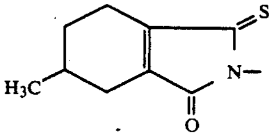 | F | $-CH_2CH_2-O-CH_2CH_2-O-C_2H_5$ |
| 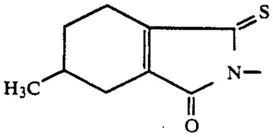 | H | $-CH_2CH_2-O-CH_2CH_2-O-C_4H_9$ |
| 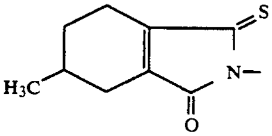 | Cl | $-CH_2CH_2-O-CH_2CH_2-O-CH_3$ |
| 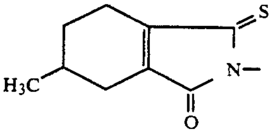 | Cl | $-CH_2CH_2-O-CH_2CH_2-O-C_2H_5$ |
| 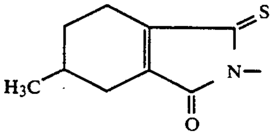 | Cl | $-CH_2CH_2-O-CH_2CH_2-O-C_3H_7$ |
| 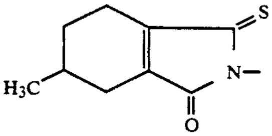 | Cl | 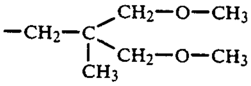 |
| 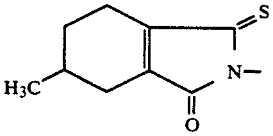 | Cl | 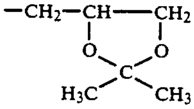 |
| 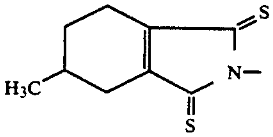 | F | $-CH_2CH_2-O-CH_2CH_2-O-C_3H_7$ |
| 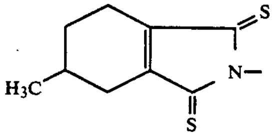 | H | $-CH_2CH_2-O-CH_2CH_2-O-C_4H_9$ |

TABLE 1-continued
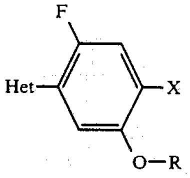
(I)
Examples of the compounds of the formula (I)
| Het | X | R |
|---|---|---|
| 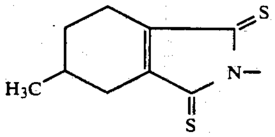 | Cl | $-CH_2CH_2-O-CH_2CH_2-O-CH_3$ |
| 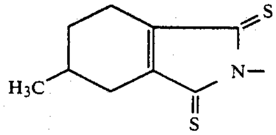 | Cl | $-CH_2CH_2-O-CH_2CH_2-O-C_2H_5$ |
| 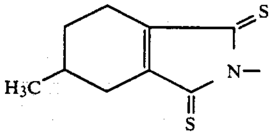 | Cl | $-CH_2CH_2-O-CH_2CH_2-O-C_3H_7$ |
| 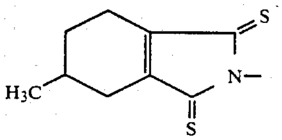 | Cl | 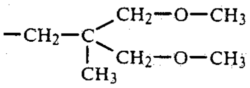 |
| 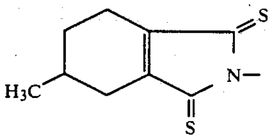 | Cl | 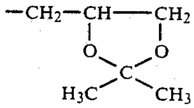 |
| 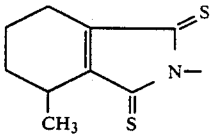 | F | $-CH_2CH_2-O-CH_2CH_2-O-C_2H_5$ |
| 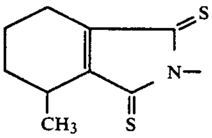 | H | $-CH_2CH_2-O-CH_2CH_2-O-C_4H_9$ |
| 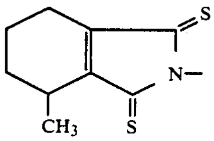 | Cl | $-CH_2CH_2-O-CH_2CH_2-O-CH_3$ |
| 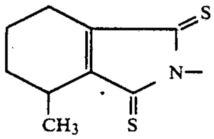 | Cl | $-CH_2CH_2-O-CH_2CH_2-O-C_2H_5$ |

TABLE 1-continued
(I)
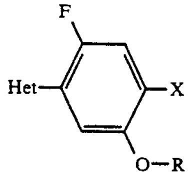
Examples of the compounds of the formula (I)
| Het | X | R |
|---|---|---|
| 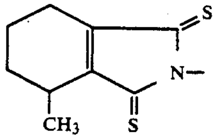 | Cl | $-CH_2CH_2-O-CH_2CH_2-O-C_3H_7$ |
| 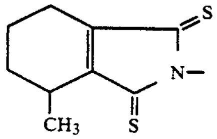 | Cl | 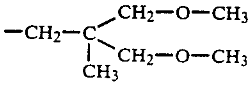 |
| 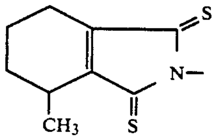 | Cl | 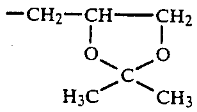 |
| 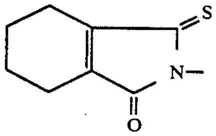 | F | $-CH_2CH_2-O-CH_2CH_2-O-C_2H_5$ |
| 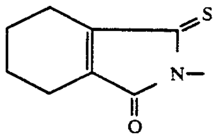 | H | $-CH_2CH_2-O-CH_2CH_2-O-C_3H_7$ |
| 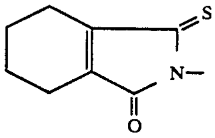 | Cl | $-CH_2CH_2-O-CH_2CH_2-O-CH_3$ |
| 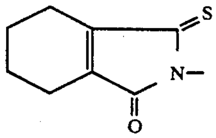 | Cl | $-CH_2CH_2-O-CH_2CH_2-O-C_2H_5$ |
| 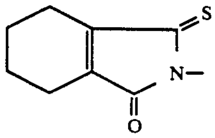 | Cl | $-CH_2CH_2-O-CH_2CH_2-O-C_3H_7$ |
| 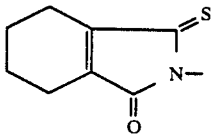 | Cl | 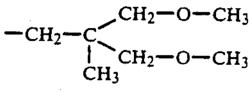 |

TABLE 1-continued
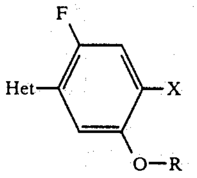
(I)
Examples of the compounds of the formula (I)
| Het | X | R |
|---|---|---|
| 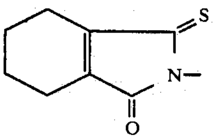 | Cl | 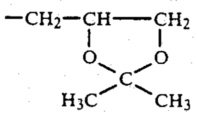 |
| 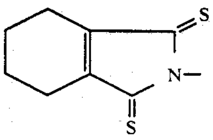 | Cl | $-CH_2CH_2-O-CH_2CH_2-O-CH_3$ |
| 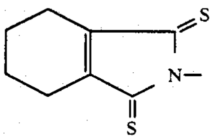 | Cl | $-CH_2CH_2-O-CH_2CH_2-O-C_2H_5$ |
| 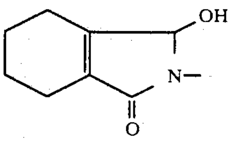 | H | $-CH_2CH_2-O-CH_2CH_2-O-C_2H_5$ |
| 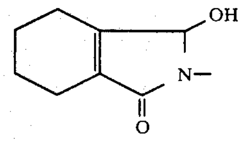 | F | $-CH_2CH_2-O-CH_2CH_2-O-C_4H_9$ |
| 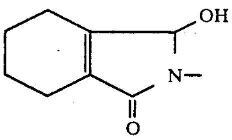 | Cl | $-CH_2CH_2-O-CH_2CH_2-O-CH_3$ |
| 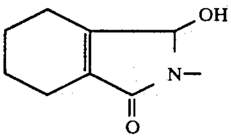 | Cl | $-CH_2CH_2-O-CH_2CH_2-O-C_2H_5$ |
| 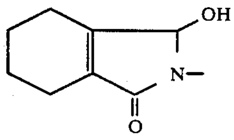 | Cl | $-CH_2CH_2-O-CH_2CH_2-O-C_3H_7$ |
| 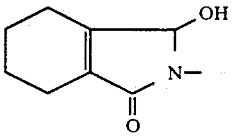 | Cl | 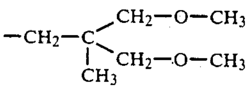 |

TABLE 1-continued
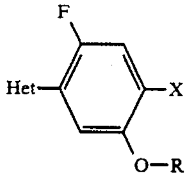
(I)
Examples of the compounds of the formula (I)
| Het | X | R |
|---|---|---|
| 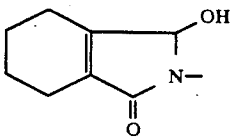 | Cl | 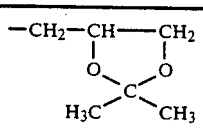 |
| 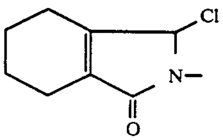 | H | $-CH_2CH_2-O-CH_2CH_2-O-C_4H_9$ |
| 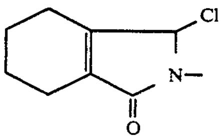 | H | $-CH_2CH_2-O-CH_2CH_2-O-C_2H_5$ |
| 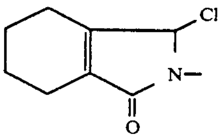 | F | $-CH_2CH_2-O-CH_2CH_2-O-C_2H_5$ |
| 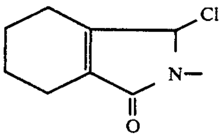 | Cl | $-CH_2CH_2-O-CH_2CH_2-O-CH_3$ |
| 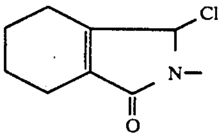 | Cl | $-CH_2CH_2-O-CH_2CH_2-O-C_2H_5$ |
| 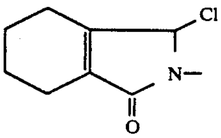 | Cl | $-CH_2CH_2-O-CH_2CH_2-O-C_3H_7$ |
| 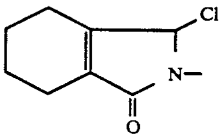 | Cl | 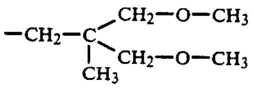 |

TABLE 1
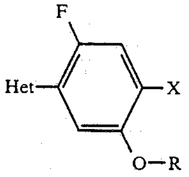
(I)
Examples of the compounds of the formula (I)
| Het | X | R |
|---|---|---|
| 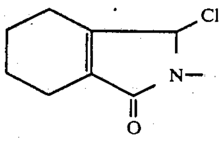 | Cl | 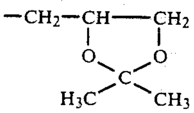 |
| 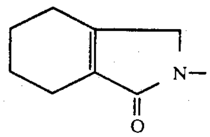 | H | $-CH_2CH_2-O-CH_2CH_2-O-C_3H_7$ |
| 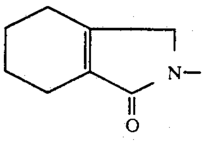 | F | $-CH_2CH_2-O-CH_2CH_2-O-C_4H_9$ |
| 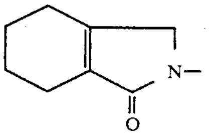 | Cl | $-CH_2CH_2-O-CH_2CH_2-O-CH_3$ |
| 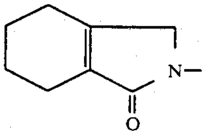 | Cl | $-CH_2CH_2-O-CH_2CH_2-O-C_2H_5$ |
| 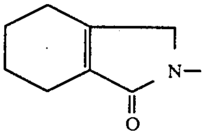 | Cl | 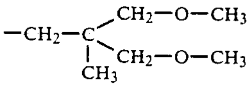 |
| 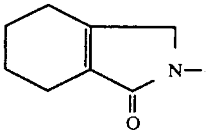 | Cl | 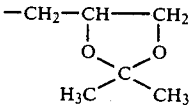 |
| 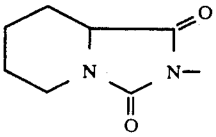 | H | $-CH_2CH_2-O-CH_2CH_2-O-C_2H_5$ |
| 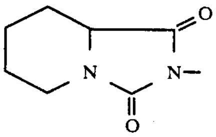 | H | $-CH_2CH_2-O-CH_2CH_2-O-C_4H_9$ |

TABLE 1-continued
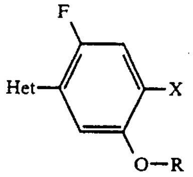
(I)
Examples of the compounds of the formula (I)
| Het | X | R |
|---|---|---|
| 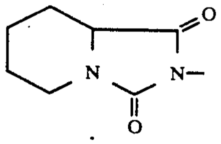 | F | $-CH_2CH_2-O-CH_2CH_2-O-C_2H_5$ |
| 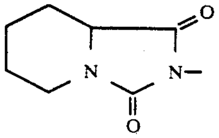 | F | $-CH_2CH_2-O-CH_2CH_2-O-CH_3$ |
| 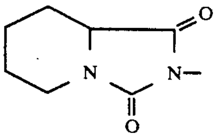 | Cl | $-CH_2CH_2-O-CH_2CH_2-O-CH_3$ |
| 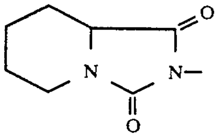 | Cl | $-CH_2CH_2-O-CH_2CH_2-O-C_2H_5$ |
| 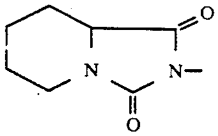 | Cl | $-CH_2CH_2-O-CH_2CH_2-O-C_3H_7$ |
| 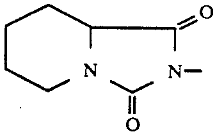 | Cl | $-CH_2CH_2-O-CH_2CH_2-O-C_4H_9$ |
| 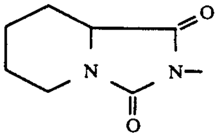 | Br | $-CH_2CH_2-O-CH_2CH_2-O-C_2H_5$ |
| 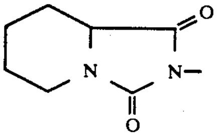 | Br | $-CH_2CH_2-O-CH_2CH_2-O-CH_3$ |
| 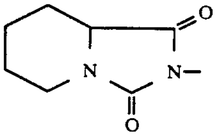 | Cl | 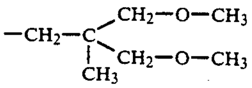 |

TABLE 1-continued
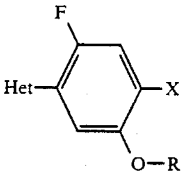
(I)
Examples of the compounds of the formula (I)
| Het | X | R |
| --- | --- | --- |
| 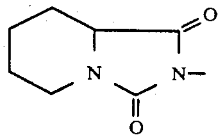 | Cl | 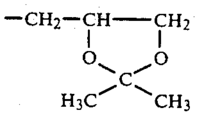 |
| 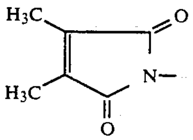 | H | $-CH_2CH_2-O-CH_2CH_2-O-C_2H_5$ |
| 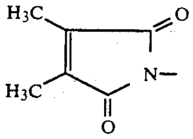 | F | $-CH_2CH_2-O-CH_2CH_2-O-C_2H_5$ |
| 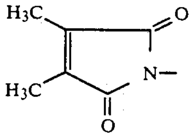 | Cl | $-CH_2CH_2-O-CH_2CH_2-O-CH_3$ |
| 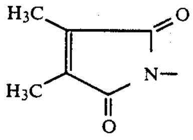 | Cl | $-CH_2CH_2-O-CH_2CH_2-O-C_2H_5$ |
| 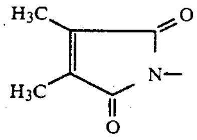 | Cl | $-CH_2CH_2-O-CH_2CH_2-O-C_3H_7$ |
| 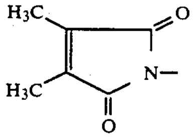 | Cl | $-CH_2CH_2-O-CH_2CH_2-O-C_4H_9$ |
| 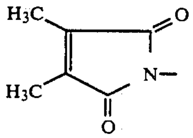 | Br | $-CH_2CH_2-O-CH_2CH_2-O-CH_3$ |
| 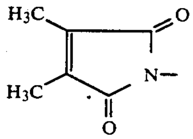 | Br | $-CH_2CH_2-O-CH_2CH_2-O-C_2H_5$ |

TABLE 1-continued
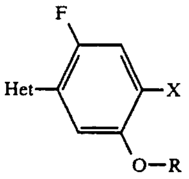
(I)
Examples of the compounds of the formula (I)
| Het | X | R |
|---|---|---|
| 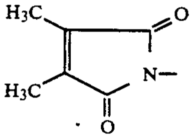 | Cl | 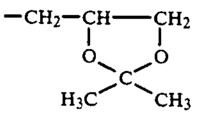 |
| 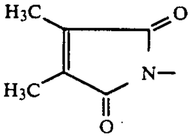 | Cl | 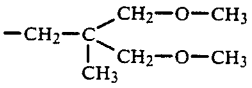 |
| 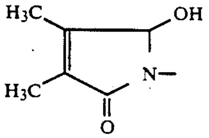 | H | $-CH_2CH_2-O-CH_2CH_2-O-C_2H_5$ |
| 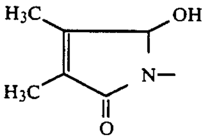 | F | $-CH_2CH_2-O-CH_2CH_2-O-C_2H_5$ |
| 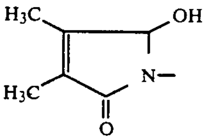 | Cl | $-CH_2CH_2-O-CH_2CH_2-O-CH_3$ |
| 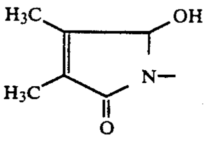 | Cl | $-CH_2CH_2-O-CH_2CH_2-O-C_2H_5$ |
| 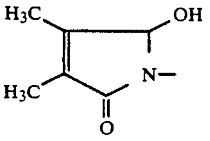 | Cl | $-CH_2CH_2-O-CH_2CH_2-O-C_3H_7$ |
| 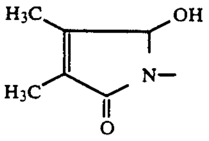 | Cl | $-CH_2CH_2-O-CH_2CH_2-O-C_4H_9$ |
| 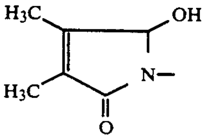 | Cl | 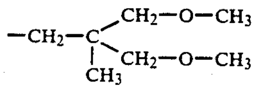 |

TABLE 1-continued
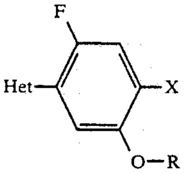
(I)
Examples of the compounds of the formula (I)
| Het | X | R |
|---|---|---|
| 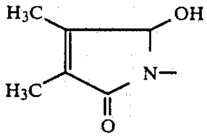 | Cl | 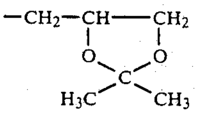 |
| 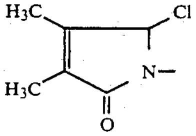 | H | $-CH_2CH_2-O-CH_2CH_2-O-CH_3$ |
| 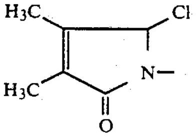 | F | $-CH_2CH_2-O-CH_2CH_2-O-C_4H_9$ |
| 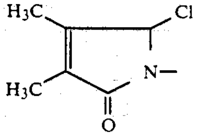 | Cl | $-CH_2CH_2-O-CH_2CH_2-O-CH_3$ |
| 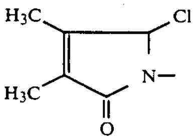 | Cl | $-CH_2CH_2-O-CH_2CH_2-O-C_2H_5$ |
| 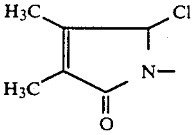 | Cl | $-CH_2CH_2-O-CH_2CH_2-O-C_4H_9$ |
| 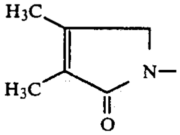 | H | $-CH_2CH_2-O-CH_2CH_2-O-C_4H_9$ |
| 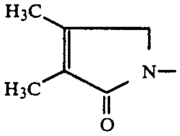 | F | $-CH_2CH_2-O-CH_2CH_2-O-C_2H_5$ |
| 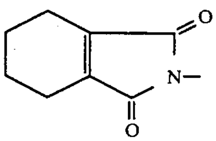 | Cl | 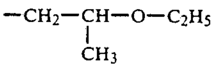 |

TABLE 1-continued
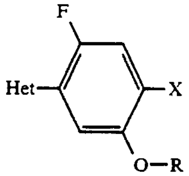
(I)
Examples of the compounds of the formula (I)
| Het | X | R |
|---|---|---|
| 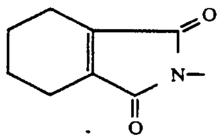 | Br | 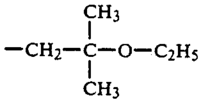 |
| 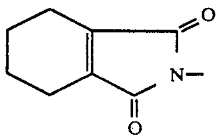 | H | 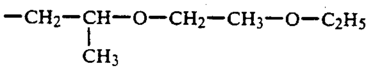 |
| 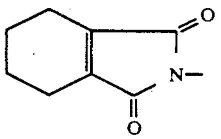 | Br | 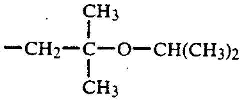 |
| 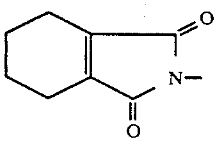 | H | 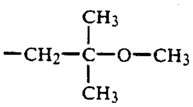 |
| 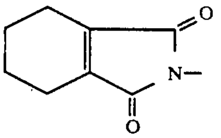 | Cl | 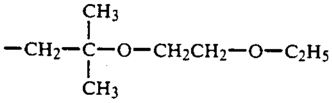 |
| 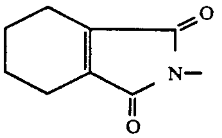 | Cl | 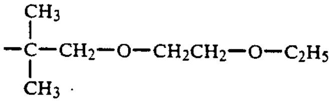 |
| 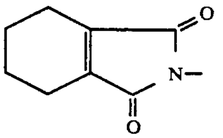 | Cl | 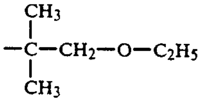 |
| 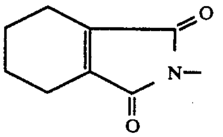 | Cl | 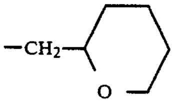 |
| 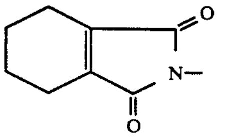 | Cl | 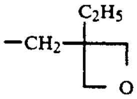 |

TABLE 1-continued
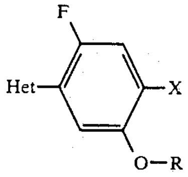
(I)
Examples of the compounds of the formula (I)
| Het | X | R |
|---|---|---|
| 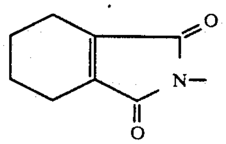 | Cl | 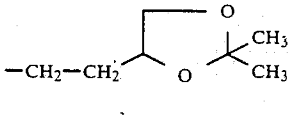 |
| 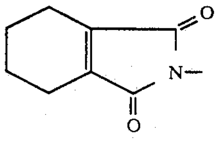 | Cl | $-CH_2-C(CH_2-O-CH_3)_3$ |
| 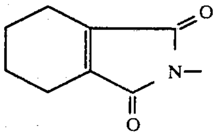 | Br | $-CH_2-C(CH_2-O-C_2H_5)_3$ |
| 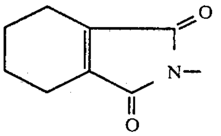 | F | 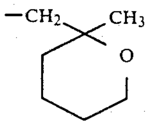 |
| 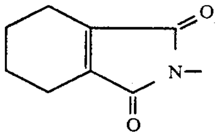 | F | 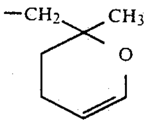 |
| 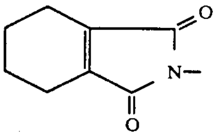 | Cl | $-CH_2-\underset{CH_3}{\underset{\vert}{CH}}-O-CH_2-CH_2-O-CH_3$ |
| 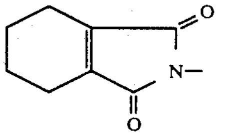 | Br | $-CH_2-CH-OCH_2CH_2-OCH_2CH_2-O-C_2H_5$ |
| 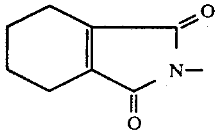 | Cl | $-CH_2-\underset{CH_2}{\underset{\Vert}{C}}-CH_2-O-CH(CH_3)_2$ |
| 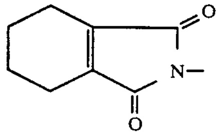 | Cl | $-\underset{CH_3}{\underset{\vert}{CH}}-\underset{CH_2}{\underset{\Vert}{C}}-CH_2-O-C_2H_5$ |

TABLE 1-continued
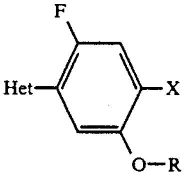
(I)
Examples of the compounds of the formula (I)
| Het | X | R |
|---|---|---|
| 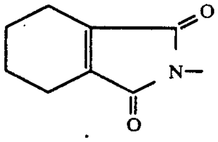 | Cl | $-CH_2-C(=CH_2)-CH_2-O-C_2H_5$ |
| 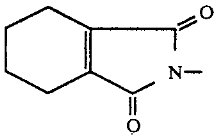 | H | 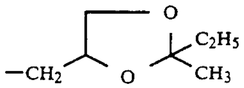 |
| 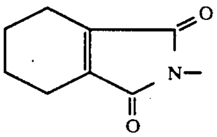 | Cl | 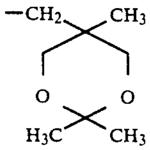 |
| 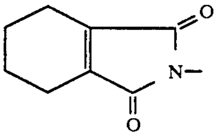 | Br | $-CH_2-CH_2-C(CH_3)_2-O-CH_3$ |
| 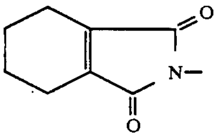 | F | $-CH_2-CH_2-C(CH_3)_2-O-CH_2-CH_2-CH(CH_3)-OCH_3$ |
| 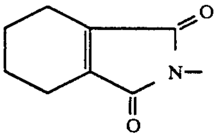 | Cl | $-CH(C_2H_5)-CH_2-O-CH_2-CH_2-O-C_2H_5$ |
| 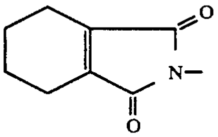 | F | $-CH(CH_3)-CH(CH_3)-O-C_2H_5$ |
| 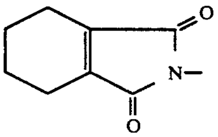 | Cl | $-CH(CH_3)-CH(CH_3)-O-CH_2-CH_2-O-C_2H_5$ |
| 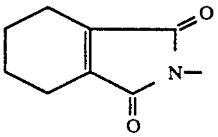 | Cl | $-CH_2-CH_2-O-CH(CH_3)-CH_2-O-C_2H_5$ |

TABLE 1-continued
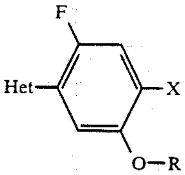 (I)
| Het | X | R |
|---|---|---|
| 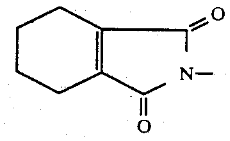 | Cl | $-CH_2-CH_2-CH-O-CH_3$<br>$CH_3$ |
| 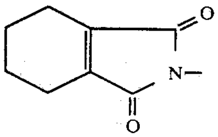 | Br | $-CH_2-CH-CH_2-O-CH_3$<br>$CH_3$ |
| 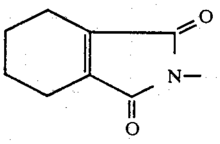 | Cl | $-CH_2-CH-O-(CH_2)_2-CH_3$<br>$CH_3$ |
| 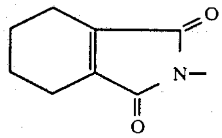 | Cl | $-CH_2-CH-O-(CH_2)_4-CH_3$<br>$CH_3$ |
| 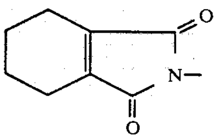 | Br | $-CH-CH_2-O-CH(CH_3)_2$<br>$CH_3$ |
| 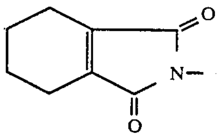 | F | $-CH-CH_2-O-C_2H_5$<br>$CH_3$ |
| 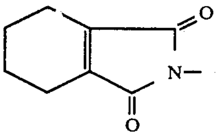 | Cl | $-O-CH-CH_2-O-C_2H_5$<br>$C_2H_5$ |
| 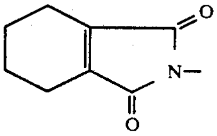 | Cl | $-CH-CH_2-O-CH_2-CH_2-O-C_2H_5$<br>$CH_3$ |
| 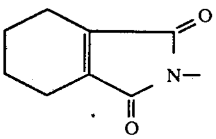 | Cl | $CH_3$<br>$-CH_2-C-CH_2-O-CH_3$<br>$CH_3$ |
Examples of the compounds of the formula (I)

TABLE 1-continued
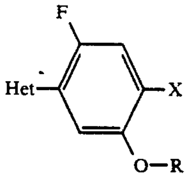
(I)
Examples of the compounds of the formula (I)
| Het | X | R |
| --- | --- | --- |
| 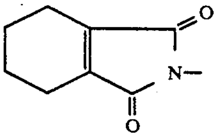 | Cl | 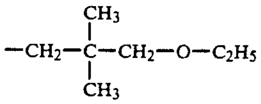 |
| 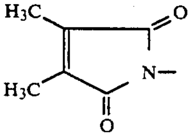 | Br | 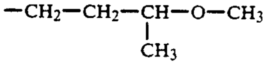 |
| 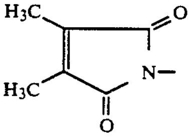 | Br | 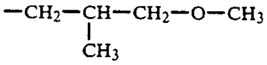 |
| 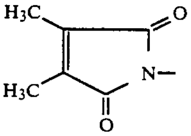 | Cl | 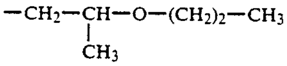 |
| 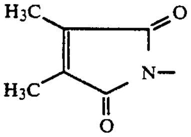 | Cl | $-CH_2-CH-O-(CH_2)_4-CH_3$ |
| 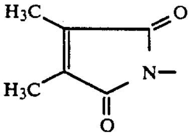 | Br | 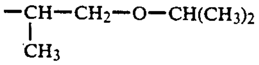 |
| 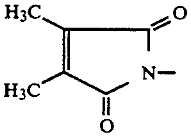 | F | 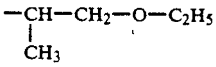 |
| 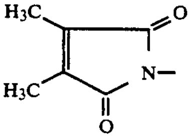 | Cl | 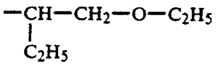 |
| 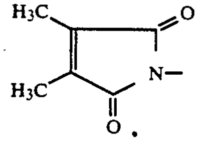 | Cl | 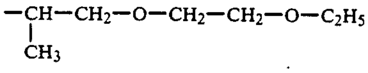 |

TABLE 1-continued
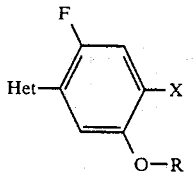
(I)
Examples of the compounds of the formula (I)
| Het | X | R |
| --- | --- | --- |
| 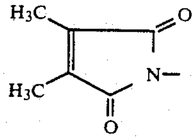 | Cl | 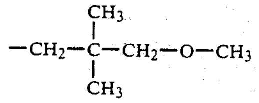 |
| 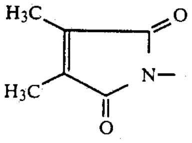 | Cl | 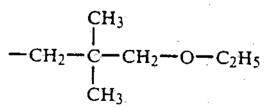 |
| 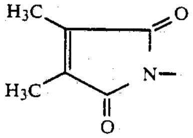 | H | 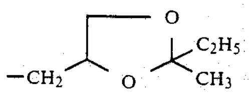 |
| 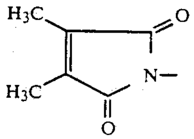 | Cl | 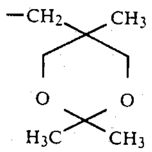 |
| 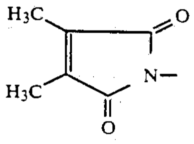 | Br | 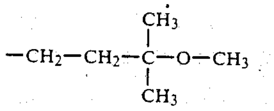 |
| 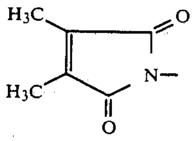 | F | 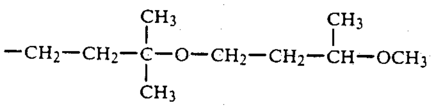 |
| 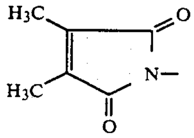 | Cl | 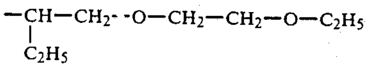 |
| 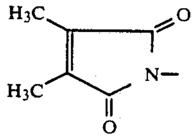 | F | 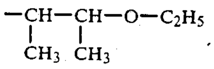 |
| 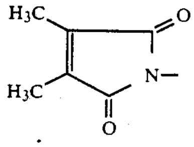 | Cl | 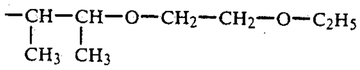 |

TABLE 1-continued
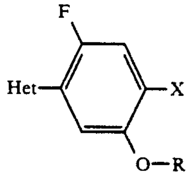
(I)
Examples of the compounds of the formula (I)
| Het | X | R |
| --- | --- | --- |
| 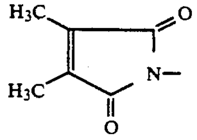 | Cl | $-CH_2-CH_2-O-\underset{CH_3}{\underset{\vert}{CH}}-CH_2-O-C_2H_5$ |
| 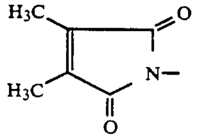 | Cl | 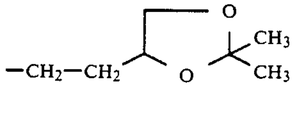 |
| 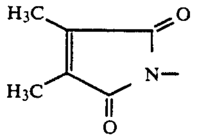 | Cl | $-CH_2-C(CH_2-O-CH_3)_3$ |
| 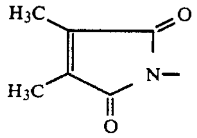 | Br | $-CH_2-C(CH_2-O-C_2H_5)_3$ |
| 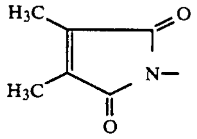 | F | 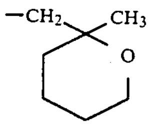 |
| 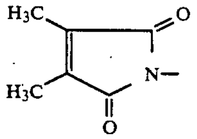 | F | 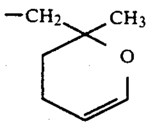 |
| 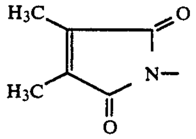 | Cl | $-CH_2-\underset{CH_3}{\underset{\vert}{CH}}-O-CH_2-CH_2-O-CH_3$ |
| 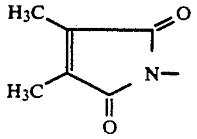 | Br | $-CH_2-\underset{CH_3}{\underset{\vert}{CH}}-OCH_2CH_2-OCH_2CH_2-OC_2H_5$ |
| 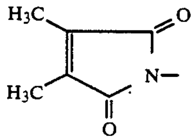 | Cl | $-CH_2-\underset{CH_2}{\underset{\Vert}{C}}-CH_2-O-CH(CH_3)_2$ |

TABLE 1-continued
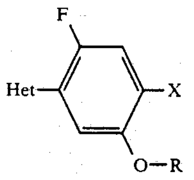
(I)
Examples of the compounds of the formula (I)
| Het | X | R |
|---|---|---|
| 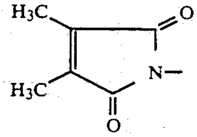 | Cl | 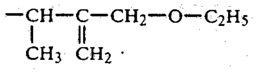 |
| 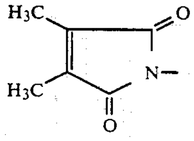 | Cl | 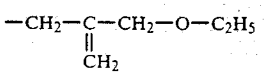 |
| 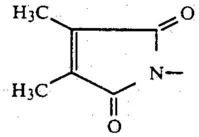 | Cl | 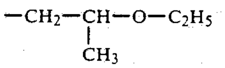 |
| 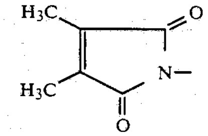 | Br | 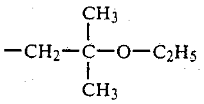 |
| 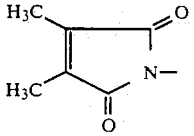 | H | 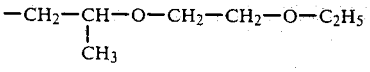 |
| 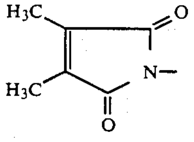 | Br | 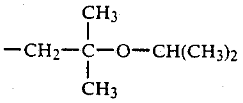 |
| 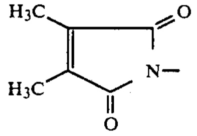 | H | 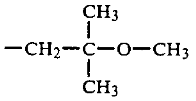 |
| 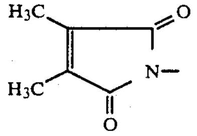 | Cl | 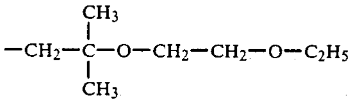 |
| 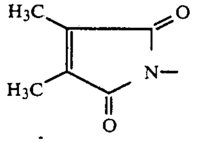 | Cl | 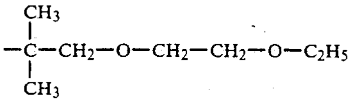 |

TABLE 1-continued
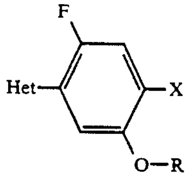
(I)
Examples of the compounds of the formula (I)
| Het | X | R |
| --- | --- | --- |
| 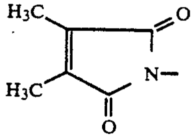 | Cl | 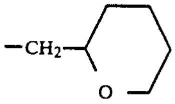 |
| 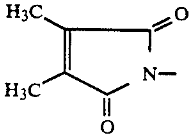 | Cl | 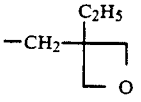 |
| 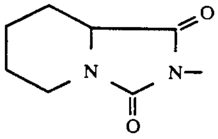 | Br | $-CH_2-CH_2-\underset{CH_3}{CH}-O-CH_3$ |
| 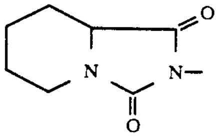 | Br | $-CH_2-\underset{CH_3}{CH}-CH_2-O-CH_3$ |
| 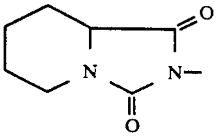 | Cl | $-CH_2-\underset{CH_3}{CH}-O-(CH_2)_2-CH_3$ |
| 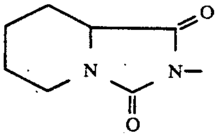 | Cl | $-CH_2-\underset{CH_3}{CH}-O-(CH_2)_4-CH_3$ |
| 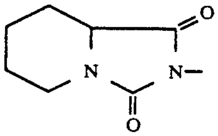 | Br | $-\underset{CH_3}{CH}-CH_2-O-CH(CH_3)_2$ |
| 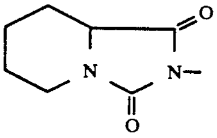 | F | $-\underset{CH_3}{CH}-CH_2-O-C_2H_5$ |
| 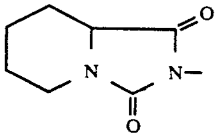 | Cl | $-\underset{C_2H_5}{CH}-CH_2-O-C_2H_5$ |

TABLE 1-continued
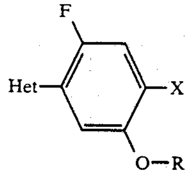
(I)
Examples of the compounds of the formula (I)
| Het | X | R |
|---|---|---|
| 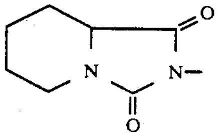 | Cl | 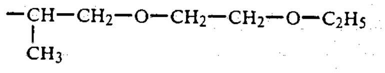 |
| 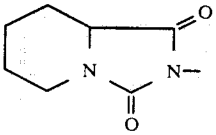 | Cl | 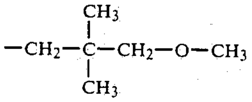 |
| 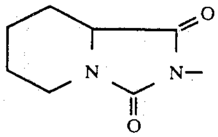 | Cl | 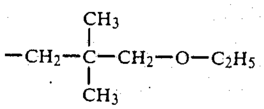 |
| 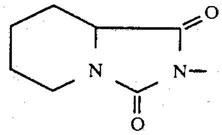 | H | 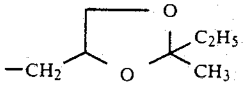 |
| 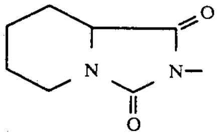 | Cl | 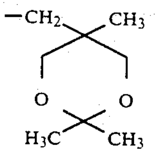 |
| 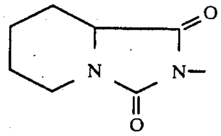 | Br | 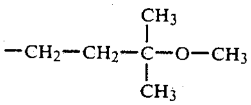 |
| 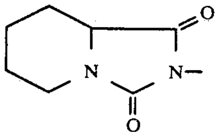 | F | 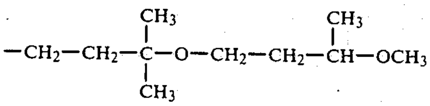 |
| 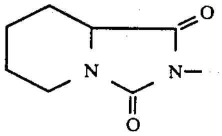 | Cl | 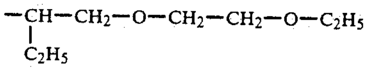 |
| 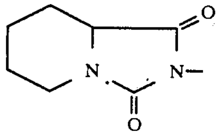 | F | 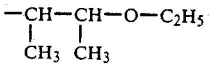 |

TABLE 1-continued
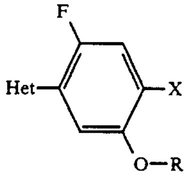
(I)
Examples of the compounds of the formula (I)
| Het | X | R |
| --- | --- | --- |
| 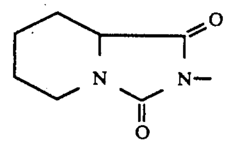 | Cl | $-CH-CH-O-CH_2-CH_2-O-C_2H_5$<br>$CH_3$ $CH_3$ |
| 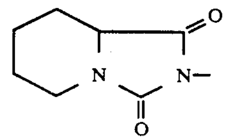 | Cl | $-CH_2-CH_2-O-CH-CH_2-O-C_2H_5$<br>$CH_3$ |
| 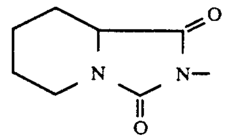 | Cl | 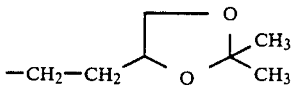 |
| 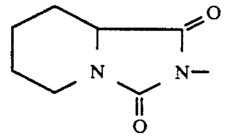 | Cl | $-CH_2-C(CH_2-O-CH_3)_3$ |
| 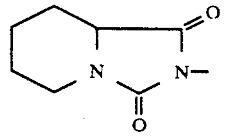 | Br | $-CH_2-C(CH_2-O-C_2H_5)_3$ |
| 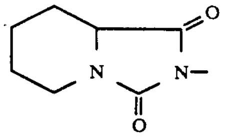 | F | 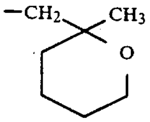 |
| 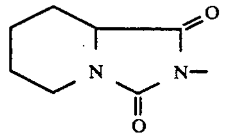 | F | 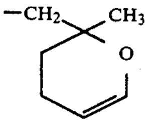 |
| 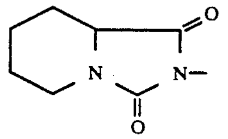 | Cl | $-CH_2-CH-O-CH_2-CH_2-O-CH_3$<br>$CH_3$ |
| 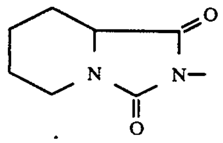 | Br | $-CH_2-CH-OCH_2CH_2-OCH_2CH_2-OC_2H_5$<br>$CH_3$ |

TABLE 1-continued
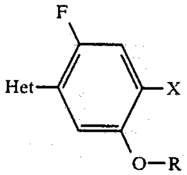
(I)
Examples of the compounds of the formula (I)
| Het | X | R |
|---|---|---|
| 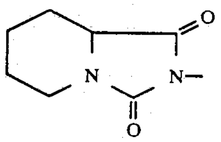 | Cl | 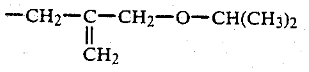 |
| 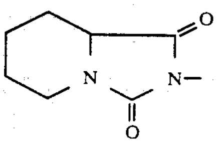 | Cl | 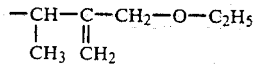 |
| 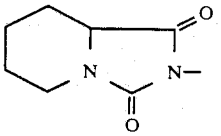 | Cl | 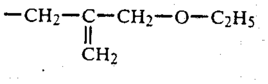 |
| 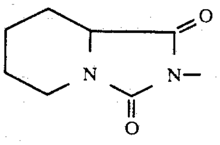 | Cl | 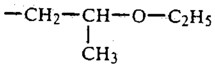 |
| 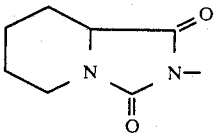 | Br | 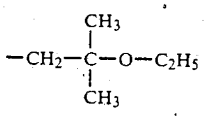 |
| 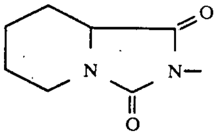 | H | 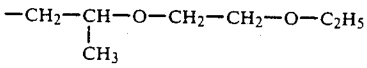 |
| 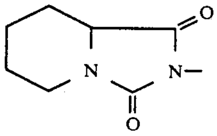 | Br | 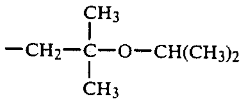 |
| 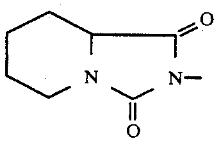 | H | 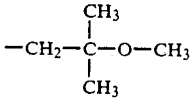 |
| 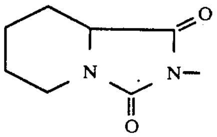 | Cl | 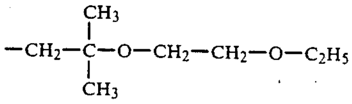 |

TABLE 1-continued

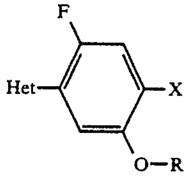

(I)

Examples of the compounds of the formula (I)

| Het | X | R |
|---|---|---|
| 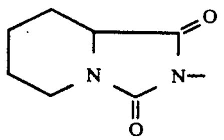 | Cl | 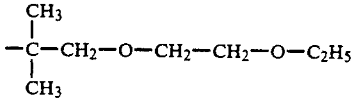 |
| 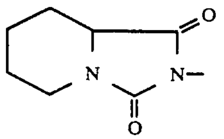 | Cl | 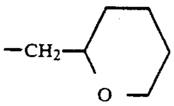 |
| 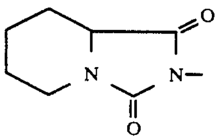 | Cl | 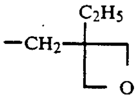 |

If, for example, 3,4,5,6-tetrahydrophthalic anhydride and 2,4-difluoro-5-(2-2-methoxy-ethoxy)-ethoxy)-aniline are used as starting substances, the course of the reaction in process (a) according to the invention can be represented by the following equation:

If, for example, N-(4-bromo-2-fluoro-5-(2-(2-ethoxy-ethoxy)-ethoxy)-phenyl)-dimethyl-maleimide and sodium borohydride are used as starting substances, the course of the reaction in process (b) according to the invention can be represented by the following equation:

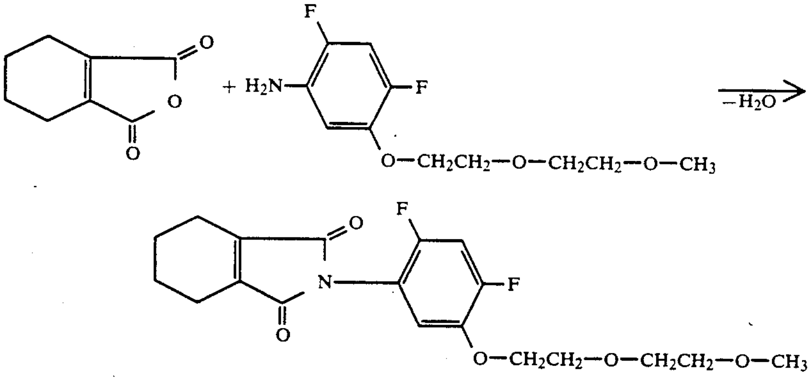

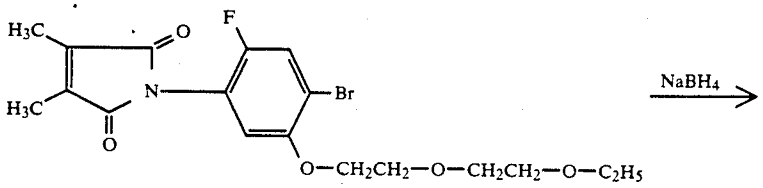

-continued

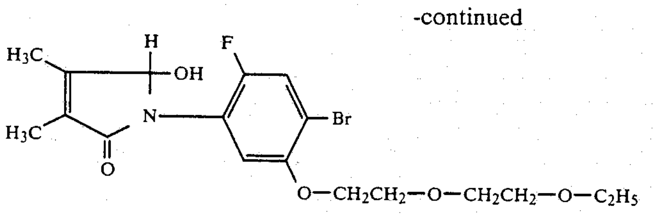

If, for example, N-(4-chloro-2-fluoro-5-(2,2-bismethoxymethyl-propyl)-phenyl)-3,4,5,6-tetrahydrophthalimide and phosphorous(V) sulphide are used as starting substances, the course of the reaction in process (c) according to the invention can be represented by the following equation:

If, for example, N-(4-chloro-2-fluoro-(5-(2-(2-propoxy-ethoxy)-ethoxy)-phenyl)-3,4-dimethyl-$\Delta^3$pyrrolin-5-ol-2-one and thionyl chloride are used as starting substances, the course of the reaction in process (d) according to the invention may be represented by the following equation:

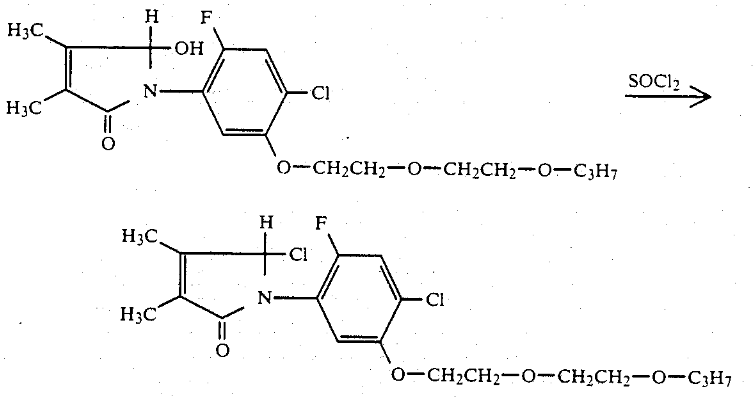

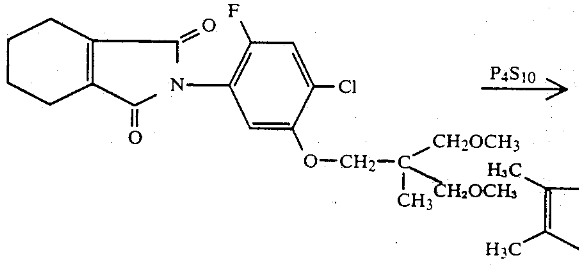

If, for example, N-(2,4-difluoro-5-(2-(2-butoxyethoxy)-ethoxy)-phenyl)-5-chloro-3,4-dimethyl-$\Delta^3$-pyrrolin-2-one is used as starting compound, the course of the reaction in process (e) according to the invention can be represented by the following equation:

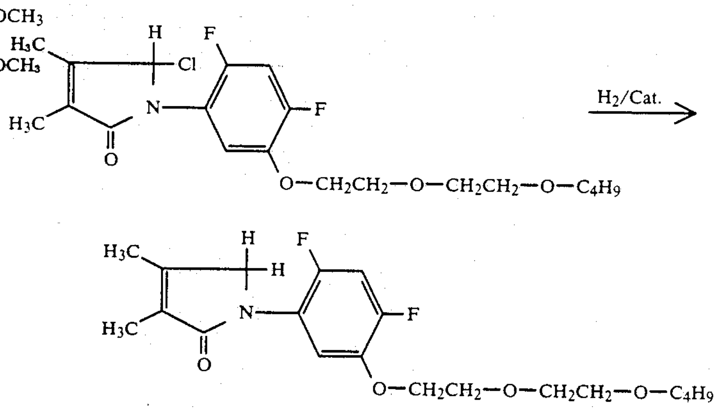

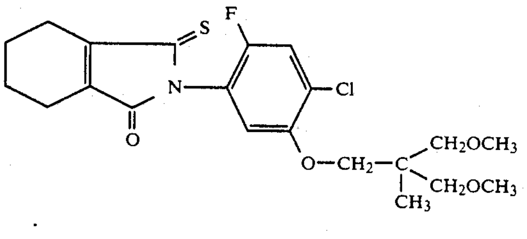

If, for example, N-(2-fluoro-5-hydroxy-phenyl)-3,4,5,6-tetrahydro-phthalimide and 2-(2-methoxy-ethoxy)-ethyl methanesulphonate are used as starting substances, the course of the reaction in process (f) according to the invention can be represented by the following equation:

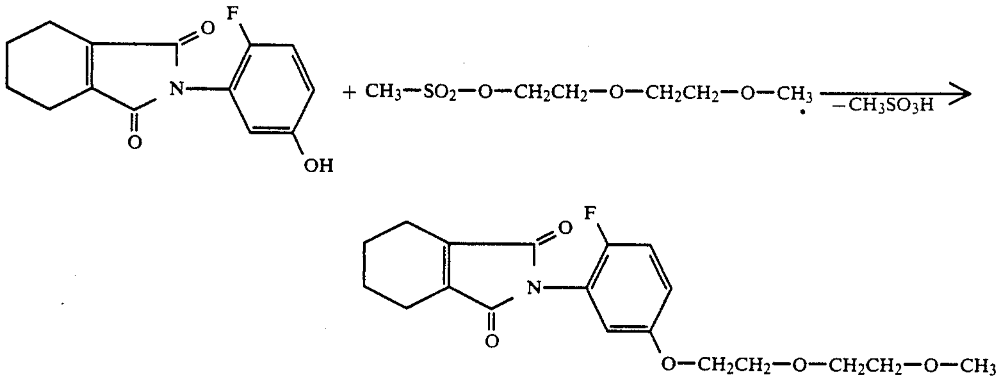

If, for example, N-(2-fluoro-5-(2-(2-ethoxy-ethoxy)-phenyl)-phthalimide and chlorine are used as starting substances, the course of the reaction in process (g) according to the invention can be represented by the following equation:

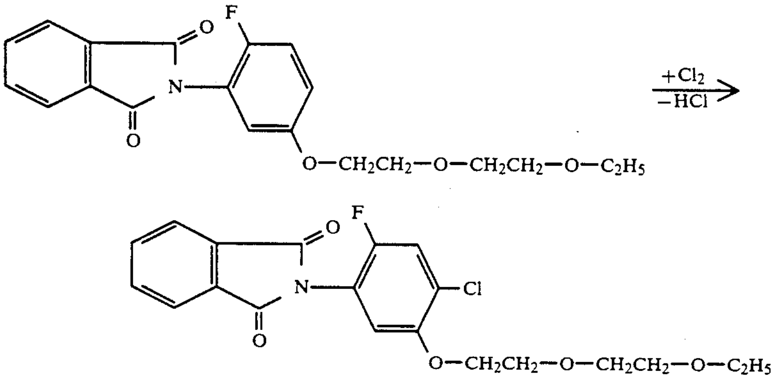

If, for example, methyl chloroformate, 4-chloro-2-fluoro-5-(2-(2-methoxy-ethoxy)-ethoxy)-aniline and ethyl piperidine-2-carboxylate are used as starting substances, the course of the reaction in process (h) according to the invention can be represented by the following equation:

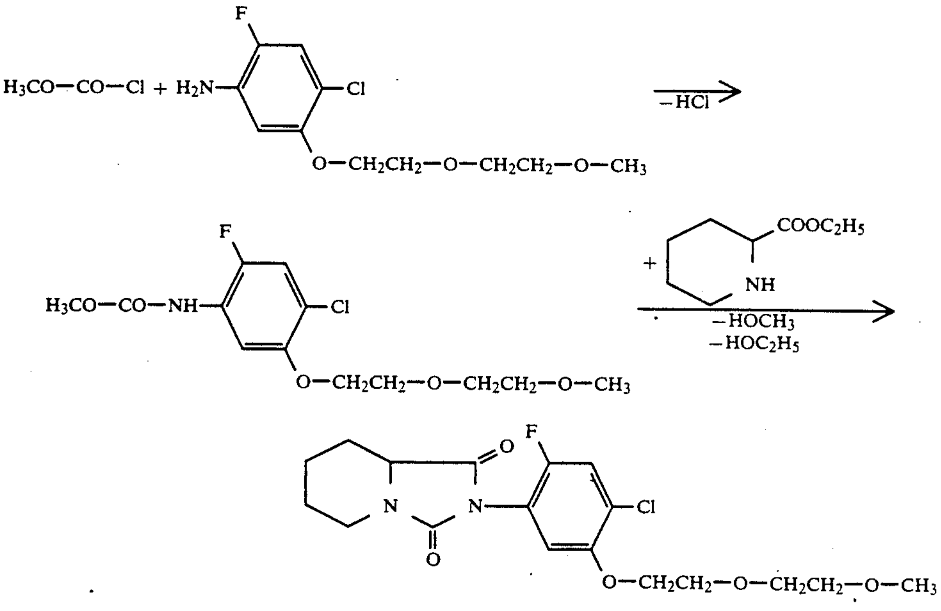

Formula (II) provides a general definition of the cyclic anhydrides to be used as starting substances in process (a) according to the invention, for the preparation of compounds of the formula (I).

In formula (II), A preferably, or in particular, has the meaning which has already been mentioned above in connection with the description of the compounds of the formula (I) according to the invention as being preferred, or particularly preferred, for A.

Examples of the starting substances of the formula (II) which may be mentioned are: phthalic anhydride, 3,4,5,6-tetrahydro-phthalic anhydride, 3-methyl-, 4-methyl-, 4-trifluoromethyl- and 3,3-dimethyl-3,4,5,6-tetrahydro-phthalic anhydride, 1,2,3,4-tetrahydro-, 1,2,3,6-tetrahydro- and 2,3,4,5-tetrahydro-phthalic anhydride, 3,6-dihydro-phthalic anhydride and dimethylmaleic anhydride.

The starting substances of the formula (II) are known chemicals for organic synthesis.

Formula (III) provides a general definition of the arylamines also to be used as starting substances in process (a) according to the invention, for the preparation of compounds of the formula (I).

In formula (III), R and X preferably, or in particular, have those meanings which have already been mentioned above in connection with the description of the compounds of the formula (I) according to the invention as being preferred, or particularly preferred, for R and X.

Examples of the starting substances of the formula (III) which may be mentioned are: 5-(2-(2-methoxy-ethoxy)-ethoxy)-, 5-(2-(2-ethoxy-ethoxy)-ethoxy)-5-(2-(2-propoxy-ethoxy)-ethoxy)-, 5-(2-(2-isopropoxy-ethoxy)-ethoxy)-, 5-(2-(2-butoxy-ethoxy)-ethoxy)-, 5-(2-(2-isobutoxy-ethoxy)-ethoxy)-, 5-(2-(2-sec-butoxyethoxy)-ethoxy)-, 5-(2-(2-tert-butoxy-ethoxy)-ethoxy)-, 5-(2,2-bis-methoxymethyl-propoxy)- and 5-((2,2-dimethyl-1,3-dioxolan-4-yl)-methoxy)-2-fluoro-aniline, -2,4-difluoro-aniline, -4-chloro-2-fluoro-aniline and -4-bromo-2-fluoro-aniline.

The starting substances of the formula (III) were hitherto unknown from the literature.

The compounds of the general formula (III) are obtained when (α) hydroxyarylamines of the general formula (IX)

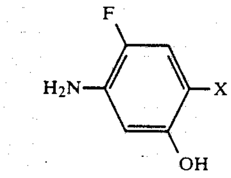

(IX)

in which

X has the abovementioned meaning, are reacted with alkylating agents of the general formula (V)

$X^1—R$ (V)

in which

R and $X^1$ have the abovementioned meanings, in the presence of a diluent, such as, for example, acetone, acetonitrile, dimethylformamide, dimethyl sulphoxide or N-methyl-pyrrolidone, if appropriate in the presence of an acid acceptor, such as, for example, sodium carbonate, potassium carbonate, sodium hydride, potassium hydride, sodium hydroxide or potassium hydroxide, and if appropriate additionally in the presence of water, at temperatures between 0° C. and 100° C., or when (β) nitrophenol derivatives of the general formula (X)

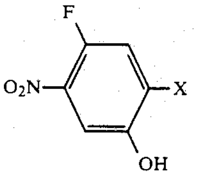

(X)

in which

X has the abovementioned meaning, are reacted with alkylating agents of the general formula (V)

$X^1—R$ (V)

in which

R and $X^1$ have the abovementioned meanings, by the technique mentioned above under (α), and the resulting compounds of the general formula (XI)

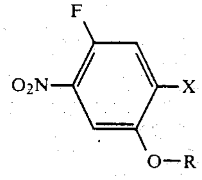

(XI)

in which

R and X have the abovementioned meanings, are reduced by customary methods, for example using hydrogen in the presence of a catalyst, such as, for example, platinum on active charcoal, in the presence of a diluent, such as, for example, ethanol, at temperatures between 0° C. and 100° C., or when (γ) fluorophenol derivatives of the general formula (XII)

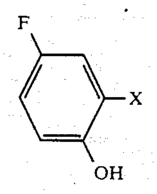

(XII)

in which

X has the abovementioned meaning, are reacted with alkylating agents of the general formula (V)

$X^1—R$ (V)

in which

R and $X^1$ have the abovementioned meanings, by the method give above under (α), and the resulting compounds of the formula (XIII)

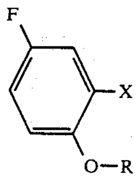

(XIII)

in which

R and X have the abovementioned meanings, are nitrated using nitric acid to give the compounds of the formula (XI), and the batch is then reduced by customary methods (see (β)).

The nitration can be carried out in inorganic acids, such as sulphuric acid or nitric acid, but also in organic solvents, preferably halogeno hydrocarbons, such as methylene chloride, with or without the addition of salts of nitrous acid, with or without the addition of urea or amidosulphonic acid, at temperatures from −30° C. to +60° C., preferably −10° C. to +30° C.

The hydroxylarylamines of the formula (IX), the nitrophenol derivatives of the formula (X) and the phenols of the formula (XII), which are known as starting substances, have already been disclosed (cf. EP-A 61,741). Examples of these compounds which may be mentioned are: 2-chloro-4-fluorophenol and 4-fluorophenol, 2-fluoro-3-hydroxy-aniline and -nitrobenzene, 4-chloro-2-fluoro-3-hydroxy-aniline and -nitrobenzene and also 4-bromo-2-fluoro-3-hydroxy-aniline and -nitrobenzene.

Formula (V) provides a general definition of the alkylating agents also required as starting substances.

In formula (V), R preferably, or in particular, has the meaning which has already been mentioned above in connection with the description of the compounds of the formula (I) according to the invention as being preferred, or particularly preferred, for R, and $X^1$ preferably stands for methylsulphonyl, phenylsulphonyl or tolylsulphonyl.

Examples of the starting substances of the formula (V) which may be mentioned are: the 2-(2-methoxy-ethoxy)-ethyl ester, the 2-(2-ethoxy-ethoxy)-ethyl ester, the 2-(2-propoxy-ethoxy)-ethyl ester, the 2-(2-butoxy-ethoxy)-ethyl ester, the 2-(2-isopropoxyethoxy)-ethyl ester, the 2-(2-isobutoxy-ethoxy)-ethyl ester, the 2-(2-sec-butoxy-ethoxy)-ethyl ester, the 2-(2-tert-butoxy-ethoxy)-ethyl ester, the 2,2-bis-methoxymethylpropyl ester and (2,2-dimethyl-1,3-dioxolan-4-yl)-methyl ester of methanesulphonic acid, benzenesulphonic acid and p-toluenesulphonic acid.

The alkylating agents of the formula (V) are known and/or can be prepared by processes known per se, for example by reacting suitable sulphonyl chlorides, such as, for example, methanesulphonyl chloride, with suitable hydroxy compounds (HOR).

Formula (Ia) provides a general definition of the substituted arylimides to be used as starting substances in processes (b) and (c) according to the invention, for the preparation of compounds of the formula (I).

In formula (Ia), A, R and X preferably, or in particular, have those meanings which have already been mentioned above in connection with the description of the compounds of the formula (I) according to the invention as being preferred, or particularly preferred, for A, R and X.

Examples of the starting substances of the formula (Ia) can be seen in Table 1 (above).

The substituted arylimides of the formula (Ia) are novel compounds according to the invention; they can be prepared by process (a) according to the invention.

Formula (Ib) provides a general definition of the N-aryl nitrogen heterocyles to be used as starting substances in process (d) according to the invention; for the preparation of compounds of the formula (I).

In formula (Ib), A, R and X preferably, or in particular, have those meanings which have already been mentioned above in connection with the description of the compounds of the formula (I) according to the invention as being preferred, or particularly preferred, for A, R and X.

Examples of the starting substances of the formula (Ib) can be seen in Table 1 (above).

The N-aryl nitrogen heterocycles of the formula (Ib) are novel compounds according to the invention; they can be prepared by process (b) according to the invention.

Formula (Ic) provides a general definition of the N-aryl nitrogen heterocycles to be used as starting substances in process (e) according to the invention, for the preparation of compounds of the formula (I).

In formula (Ic), A, R and X preferably, or in particular, have those meanings which have already been mentioned above in connection with the description of the compounds of the formula (I) according to the invention as being preferred, or particularly preferred, for A, R and X.

Examples of the starting substances of the formula (Ic) can be seen in Table 1 (above).

The N-aryl nitrogen heterocycles of the formula (Ic) are novel compounds according to the invention; they can be prepared by process (d) according to the invention.

Formula (IV) provides a general definition of the hydroxyarylimides to be used as starting substances in process (f) according to the invention, for the preparation of compounds of the formula (I).

In formula (IV), A and X preferably, or in particular, have those meanings which have already been mentioned above in connection with the description of the compounds of the formula (I) according to the invention as being preferred, or particularly preferred, for A and X.

Examples of the starting substances of the formula (IV) which may be mentioned are:

N-(2-fluoro-5-hydroxy-phenyl)-, N-(2,4-difluoro-5-hydroxyphenyl)-, N-(4-chloro-2-fluoro-5-hydroxy-phenyl)-phthalimide, N-(2-fluoro-5-hydroxy-phenyl)-, N-(2,4-difluoro-5-hydroxy-phenyl)-, N-(4-chloro-2-fluoro-5-hydroxy-phenyl)- and N-(4-bromo-2-fluoro-5-hydroxy-phenyl)-3,4,5,6-tetrahydrophthalimide, N-(2-fluoro-5-hydroxy-phenyl)-, N-(2,4-difluoro-5-hydroxy-phenyl)-, N-(4-chloro-2-fluoro-5-hydroxy-phenyl)- and N-(2-fluoro-4-bromo-5-hydroxy-phenyl)-, -3-methyl-, -4-methyl-, -4-trifluoromethyl- and -3,3-dimethyl-3,4,5,6-tetrahydrophthalimide, N-(2-fluoro-5-hydroxyphenyl)-, N-(2,4-difluoro-5-hydroxy-phenyl)-, N-(4-chloro-2-fluoro-3-hydroxy-phenyl)- and N-(4-bromo-2-fluoro-5-hydroxy-phenyl)-3,6-dihydro-phthalimide, and also N-(2-fluoro-5-hydroxy-phenyl)-, N-(2,4-difluoro-5-hydroxyphenyl-, N-(4-chloro-2-fluoro-5-hydroxy-phenyl)- and N-(4-bromo-2-fluoro-5-hydroxy-phenyl)-dimethylmaleimide.

The starting substances of the formula (IV) are known and/or can be prepared by processes known per se (cf. EP-A 61,741).

Formula (V) provides a general definition of the alkylating agents also to be used as starting substances in process (f) according to the invention, for the preparation of compounds of the formula (I).

In formula (V), R preferably, or in particular, has the meaning which has already been mentioned above in connection with the description of the compounds of the formula (I) according to the invention as being preferred, or particularly preferred, for R, and $X^1$ preferably stands for methylsulphonyl, phenylsulphonyl or tolylsulphonyl.

Examples of the starting substances of the formula (V) have already been mentioned above in connection with the description of the starting substances in process (a) according to the invention.

Formula (Id) provides a general definition of the substituted arylimides to be used as starting substances in process (g) according to the invention, for the preparation of compounds of the formula (I).

In formula (Id), A and R preferably, or in particular, have those meanings which have already been mentioned above in connection with the description of the compounds of the formula (I) according to the invention as being preferred, or particularly preferred, for A and R.

Examples of the starting substances of the formula (Id) can be seen in Table 1 (above).

The substituted arylimides of the formula (Id) are novel compounds according to the invention, they can be prepared by process (a) according to the invention.

Formula (III) provides a general definition of the arylamines to be used as starting substances in process (h) according to the invention, for the preparation of compounds of the formula (I).

In formula (III), R and X preferably, or in particular, have those meanings which have already been mentioned above in connection with the description of the compounds of the formula (I) according to the invention as being preferred, or particularly preferred, for R and X.

Examples of the starting substances of the formula (III) and processes for their preparation were already mentioned above in connection with the description of the starting substances in process (a) according to the invention.

Formula (VI) provides a general definition of the chloroformic acid esters also to be used as starting substances in process (h) according to the invention. In formula (VI), $R^3$ preferably stands for methyl, benzyl or phenyl.

Examples of the starting substances of the formula (VI) which may be mentioned are:

methyl chloroformate, benzyl chloroformate and phenyl chloroformate.

The chloroformic acid esters of the formula (VI) are known chemicals for organic synthesis.

Formula (VIII) provides a general definition of the piperidine-2-carboxylic acid esters also to be used as starting substances in process (h) according to the invention.

In formula (VIII), $R^1$ and $R^2$ preferably, or in particular, have those meanings which have already been mentioned above in connection with the description of the compounds of the formula (I) according to the invention as being preferred, or particularly preferred, for $R^1$ and $R^2$, and $R^4$ preferably stands for methyl or ethyl.

Examples of the starting substances of the formula (VIII) which may be mentioned are:

methyl piperidine-2-carboxylate and ethyl piperidine-2-carboxylate.

The starting substances of the formula (VIII) are known chemicals for organic synthesis.

Process (a) according to the invention, for the preparation of novel compounds of the formula (I), is preferably carried out using diluents. Suitable diluents in this process are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, carboxylic acids, such as formic acid, acetic acid or propionic acid, esters, such as methyl acetate and ethyl acetate, nitriles, such as, for example, acetonitrile or propionitrile, amides, such as, for example, dimethylformamide, dimethylacetamide and N-methylpyrrolidone, and also dimethyl sulphoxide, tetramethylene sulphone and hexamethylphosphoric triamide.

If appropriate, process (a) according to the invention can be carried out in the presence of a suitable reaction auxiliary. Inorganic or organic acids, such as, for example, acetic acid or p-toluenesulphonic acid, anhydrides, such as, for example, acetic anhydride, or acid chlorides, such as acetyl chloride, are preferably used as reaction auxiliaries. It is also possible to use other customary water-eliminating agents, such as, for example, N,N'-dicyclohexylcarbodiimide, or customary acylating catalysts, such as, for example, 4-(N,N-dimethylamino)-pyridine, as reaction auxiliaries.

When carrying out process (a) according to the invention, the reaction temperatures can be varied within a relatively wide range. In general, the process is carried out at temperatures between 20° C. and 180° C., preferably at temperatures between 50° C. and 150° C.

For carrying out process (a) according to the invention, 1.0 to 1.5 moles, preferably 1.0 to 1.2 moles, of amine of the formula (III) and if appropriate 0.01 to 1.2 moles, preferably 0.1 to 1.0 mole, of reaction auxiliary are generally employed per mole of anhydride of the formula (II). The reaction is carried out and the reaction products are worked up and isolated by generally customary methods (cf. also the Preparation Examples).

Suitable reducing agents for carrying out process (b) according to the invention are all reducing agents which can customarily be used for reduction reactions of this type. Complex hydrides, such as, for example, sodium borohydride, sodium cyanoborohydride, lithium borohydride or lithium aluminum hydride are preferably used.

Suitable diluents for carrying out process (b) according to the invention are all customary organic or inorganic solvents, depending on the reducing agent used. Ethers, such as diethyl ether, dioxane or tetrahydrofuran, or alcohols, such as methanol, ethanol or propanol, are preferably used.

When carrying out process (b) according to the invention, the reaction temperatures can be varied within a relatively wide range, depending on the reducing agents used. In general, the process is carried out at temperatures between −20° C. and +150° C., preferably at temperatures between 0° C. and 120° C.

For carrying out process (b) according to the invention, 0.1 to 2.0 moles, preferably 0.25 to 1.5 moles, of reducing agent are generally employed per mole of substituted arylimide of the formula (Ia). The reaction is carried out and the reaction products are worked up and isolated by generally customary methods (cf. also the Preparation Examples).

Suitable sulphurizing agents for carrying out process (c) according to the invention are all sulphurizing agents which can customarily be employed for sulphurizing reactions of this type. Phosphorus-sulphur compounds, such as, for example, phosphorus(V) sulphide ($P_4S_{10}$) or the so-called Lawesson reagent (2,4-bis-(4-methoxy-phenyl)-1,3-dithia-phosphetane 2,4-disulphide, are preferably used.

Suitable diluents for carrying out process (c) according to the invention are inert organic solvents. These preferably include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, and ethers, such as diethyl ether, dioxane, tetrahydrofuran or ethylene glycol dimethyl ether or ethylene glycol diethyl ether.

When carrying out process (c) according to the invention, the reaction temperatures can be varied within a relatively wide range. In general, the process is carried out at temperatures between 0° C. and 180° C., preferably at temperatures between 20° C. and 150° C.

For carrying out process (c) according to the invention, between 0.2 to 2.0 moles, preferably between 0.5 and 1.5 moles, of sulphurizing agent are generally employed per mole of arylimide of the formula (Ia).

The reaction is carried out and the reaction products are worked up and isolated by a procedure known per se (cf. Bull. Soc. Chim. Belg. 87 (1978), 223–228). In general, mixtures of monosulphurized and disulphurized products are obtained in this process, which can be separated by customary preparation methods (for example chromatography or crystallization).

Suitable diluents for carrying out process (d) according to the invention are inert organic solvents. These preferably include aliphatic, alicyclic or aromatic, optionally halogenated hydrocarbons, such as, for example benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl ether or ethylene glycol diethyl ether, or nitriles, such as acetonitrile or propionitrile.

If appropriate, process (d) according to the invention can be carried out in the presence of a suitable reaction auxiliary. Suitable reaction auxiliaries are, in particular, organic amines or amides. Pyridine, dimethylaniline or dimethylformamide are preferably used.

When carrying out process (d) according to the invention, the reaction temperatures can be varied within a relatively wide range. In general, the process is carried out at temperatures between 0° C. and 120° C., preferably at temperatures between 20° C. and 80° C.

For carrying out process (d) according to the invention, 1.0 to 5.0 moles, preferably 1.0 to 2.0 moles, of thionyl chloride and if appropriate 0.1 to 2.0 moles, preferably 0.5 to 1.5 moles, of reaction auxiliary are generally employed per mole of N-aryl nitrogen heterocycle of the formula (Ib).

The reaction is carried out and the reaction products are worked up and isolated by generally customary methods.

Suitable catalysts for carrying out process (e) according to the invention are all customary hydrogenation catalysts. Noble metal catalysts, such as, for example, platinum, platinum oxide, palladium or ruthenium, if appropriate on a suitable carrier, such as, for example, carbon or silicon dioxide, are preferably used.

Suitable diluents for carrying out process (e) according to the invention are inert organic solvents. These preferably include aliphatic or alicyclic, optionally halogenated hydrocarbons, such as, for example, benzine, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, or alcohols, such as methanol, ethanol or propanol.

If appropriate, process (e) according to the invention can be carried out in the presence of a suitable acid-binding agent. Alkali metal carbonates, such as sodium carbonate or potassium carbonate, or organic bases, such as pyridine or lutidine, are preferably used.

When carrying out process (e) according to the invention, the reaction temperatures can be varied within a relatively wide range. In general, the process is carried out at temperatures between −20° C. and 100° C., preferably at temperatures between 0° C. and 50° C.

The process according to the invention can be carried out under atmospheric pressure or under increased pressure. The process is preferably carried out under atmospheric pressure.

For carrying out process (e) according to the invention, 1.0 to 3.0 moles, preferably 1.0 to 1.5 moles, of hydrogen and if appropriate 1.0 to 3.0 moles, preferably 1.0 to 1.5 moles, of acid-binding agent are generally employed per mole of N-aryl nitrogen heterocycle of the formula (Ic). The reaction is carried out and the reaction products are worked up and isolated by generally customary methods.

Process (f) according to the invention, for the preparation of the novel compounds of the formula (I), is preferably carried out using diluents. Suitable diluents for this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in process (f) according to the invention are all acid-binding agents which can customarily be employed for reactions of this type. Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate, potassium carbonate, sodium tertbutoxide and potassium tert-butoxide, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO), are preferably suitable.

In process (f) according to the invention, the reaction temperatures can be varied within a relatively wide range. In general, the process is carried out at temperatures between 0° C. and 150° C., preferably at temperatures between 10° C. and 100° C.

Process (f) according to the invention is generally carried out under atmospheric pressure.

For carrying out process (f) according to the invention, between 1 and 2 moles, preferably between 1.1 and 1.5 moles, of alkylating agent of the formula (V) is generally employed per mole of hydroxyarylimide of the formula (IV).

The reaction is carried out and the reaction products are worked up and isolated by generally customary methods.

Suitable halogenating agents for carrying out process (g) according to the invention are the customary halogenating agents which can be used for halogenating aromatic compounds. Elemental halogens, such as chlorine or bromine, or halogen compounds, such as sulphuryl chloride, are preferably used.

If appropriate, process (g) is carried out using catalysts. Suitable catalysts are preferably acid or electrophilic halogen compounds, such as, for example, hydrogen chloride, hydrogen bromide, aluminum chloride, aluminum bromide, iron(III) chloride or iron(III) bromide.

Process (g) according to the invention is preferably carried out using diluents. Suitable diluents are above all those organic solvents which have already been mentioned above in process (f), but also acetic acid and/or water.

In process (g) according to the invention, the reaction temperatures can be varied within a relatively wide range. In general, the process is carried out at temperatures between 0° C. and 150° C., preferably at temperatures between 20° C. and 120° C.

Process (g) is generally carried out under atmospheric pressure.

For carrying out process (g) according to the invention, between 1 and 5 moles, preferably between 1 and 3 moles, of halogenating agent are generally employed per mole of starting compound of the formula (Id).

The reaction is carried out and the reaction products are worked up and isolated by generally customary methods.

Process (h) according to the invention is preferably carried out using diluents. Suitable diluents are above all those organic solvents which have already been mentioned above in process (f), and additionally, in the second step, preferably also alcohols, such as methanol, ethanol or isopropanol.

Process (h) according to the invention is preferably carried out in the presence of an acid acceptor. Suitable acid acceptors are above all those acid-binding agents which have already been mentioned above in process (f).

In process (h) according to the invention, the reaction temperatures can be varied within a relatively wide range. In general, the process is carried out at temperatures between −20° C. and +150° C., preferably at temperatures between 0° C. and 100° C.

Process (h) according to the invention is generally carried out under atmospheric pressure.

For carrying out process (h) according to the invention, between 0.8 and 1.5 moles, preferably between 1.0 and 1.2 moles, of chloroformic acid ester of the formula (VI) are generally employed per mole of arylamine of the formula (III), and between 0.8 and 1.5 moles, preferably between 1.0 and 1.2 moles, of piperidine-2-carboxylic acid of the formula (VIII) are generally employed per mole of arylurethane of the formula (VII).

The reaction is carried out and the reaction products are worked up and isolated by generally customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selectively combating dicotyledon weeds using the pre-emergence method and the post-emergence method.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted to the customary formulations, such as solutions, emulsions, wettable powders, suspensions, powders, pastes, soluble powders, granules, suspension-emulsion concentrates, natural and synthetic substances impregnated with active compound and very fine capsules in polymeric substances and in coating compositions for seed, as well as ULV formulations.

These formulations are produced in a known manner, for example by mixing the active compounds with extenders, that is, liquid solvents, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oil, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable, for example, ammonium salts, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable, for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable, for example, non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products. As dispersing agents there are suitable, for example, lignin-sulphite waste liquors and methylcellulose.

Adhesives such as carboxymethylcellulose, natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be used as such or in the form of their formulations and can also be used as mixtures with known herbicides for combating weeds, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (MEIRIBUZIN) f? r combating weeds in soy beans. 2,4-dichlorophenoxyacetic acid (2,4-D); 4-(2,4-dichlorophenoxy)-butyric acid (2,4-DB); 2,4-dichlorophenoxy propionic acid (2,4-DP); methyl 2-[[[[(4,6-dimethoxypyrimidin-2-yl)amino]-carbonyl]-amino]-sulphonyl]-methyl]-benzoate (BENSULFURON), 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxybenzonitrile (BROMOXYNIL); 2-chloro-N-{[(4-methoxy-6-methyl-1,3,5-triazin-2-yl)amino]-carbonyl}-benzenesulphonamide (CHLORSULFURON); N,N-dimethyl-N'-(3-chloro-4-methylphenyl)-urea (CHLORTOLURON); 2-[4-(2,4-dichlorophenoxy)-phenoxy]-propionic acid, its methyl ester or its ethyl ester (DICLOFOP); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)propionic acid (MCPP); N-methyl-2-(1,3-benzothiazol-2-yloxy)-acetanilide (MEFENACET); 2-{[[((4-methoxy-6-methyl-1,3,5-triazin-2-yl)-amino)-carbonyl]-amino]-sulphonyl}benzoic acid or its methyl ester (METSULFURON); S-ethyl N,N-hexamethylenethiolcarbamate (MOLINATE) 4-(di-n-propylamino)-3,5-dinitrobenzenesulphonamide (ORYZALIN) N-(1-ethylpropyl) -3,4-dimethyl-2,6-dinitro-aniline (PENDIMETHALIN); 0-(6-chloro-3-phenyl-pyridazin-4-yl) S-octyl thiocarbonate (PYRIDATE); 2,4-bis-[N-ethylamino]-6-methylthio-1,3,5-triazine (SIMETRYNE) 4-ethylamino-2-t-butylamino-6-methylthio-s-triazine (TERBUTRYNE); methyl 3-[[[[(4-methoxy-6-methyl-1,3,5-triazin-2-yl)-amino] -carbonyl]-amino]-sulphonyl]-thiophene-2-carboxylate (THIAMETURON), S-(2,3,3-trichloroallyl N,N-diisopropylthiolcarbamate (TRIALLATE) and 3,5,6-trichloro-2-pyridyloxyacetic acid (TRICLOPYR). Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

Preparation Examples

Example 1

(Process (a))

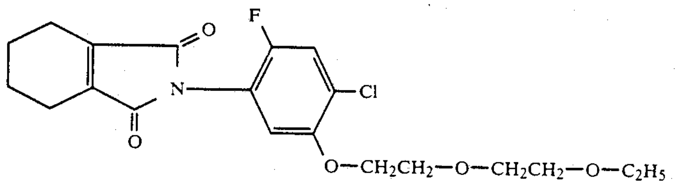

A mixture of 6.4 g (0.023 mol) of 4-chloro-2-fluoro-5-(2-(2-ethoxy-ethoxy)-ethoxy)-aniline, 3.7 g (0.024 mol) of 3,4,5,6-tetrahydrophthalic anhydride and 60 ml of acetic acid is stirred for 5 hours at 80° C. When the reaction mixture is cold, it is diluted with water and extracted using methylene chloride. The organic phase is washed using sodium bicarbonate solution, dried over magnesium sulphate and concentrated in vacuo. The resulting dark oil is subjected to purification by column chromatography on silica gel using cyclohexane/ethyl acetate (1:1) as the eluent.

4.8 g (50.7% of theory) of N-[4-chloro-2-fluoro-5-[2-(2-ethoxy-ethoxy)-ethoxy]-phenyl]-3,4,5,6-tetrahydrophthalimide are obtained as colorless crystals of melting point 61° C.

Example 2

(Process (h))

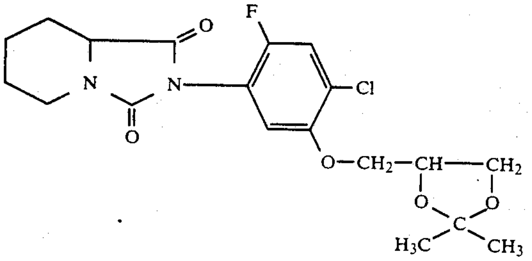

A solution of 1.4 ml (11 mmol) of phenyl chloroformate in 15 ml of methylene chloride and 15 ml of 1N sodium hydroxide solution are added simultaneously to a stirred solution of 3.05 g (11 mmol) of 4-chloro-2-fluoro-5-((2,2-dimethyl-1,3-dioxolan-4-yl)-methoxy)-aniline in 20 ml of methylene chloride, which is cooled at 0° C. to 5° C. The mixture is stirred for 30 minutes, the organic phase is then separated off and the aqueous phase is reextracted using methylene chloride; the organic phases are combined, dried using sodium sulphate and filtered. the solvent is removed from the filtrate by distillation under a waterpump vacuum, the residue is taken up in 20 ml of propanol, 1.73 g (11 mmol) of ethyl piperidine-2-carboxylate are added, and the mixture is refluxed for 6 hours. The mixture is concentrated and the residue is then taken up in methylene chloride, and this solution is washed with 1N sodium hydroxide solution, dried using sodium sulphate and filtered. The filtrate is concentrated and the residue is purified by column chromatography (on silica gel using cyclohexane/ethyl acetate, 2:3).

1.85 g (41 % of theory) of 2-(4-chloro-2-fluoro-5-((2,2-dimethyl-1,3-dioxolan-4-yl)-methoxy)-phenyl)-5,6,7,8-tetrahydroimidazo[1,5a]-pyridine-1,3(2H,8aH)-dione are obtained as an oil.

$^1$H-NMR (200 MHz, $CDCl_3$, δ): 1.40 and 1.46 (2s, 6H, 2x $CH_3$); 4.48 (m, 1H, $-OCH<$); 6.88 (d, 1H,

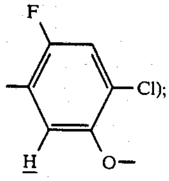 Cl); 7.29 (d, 1H, 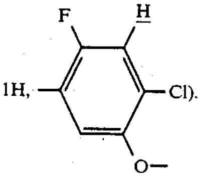 Cl).

The compounds of the formula (I) listed in Table 2 below can be obtained analogously to Example 1 or 2 and/or following the general instructions of the preparation processes according to the invention.

TABLE 2
Examples of the compounds of the formula (I)
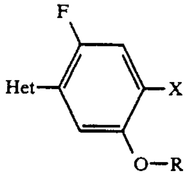
(I)
| Example No. | Het | X | R | Physical data (melting point °C.) |
|---|---|---|---|---|
| 3 | 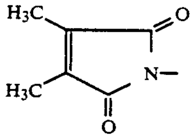 | Cl | $-CH_2CH_2-O-CH_2CH_2-O-C_2H_5$ | |
| 4 | 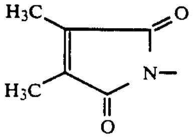 | Cl | $-CH_2CH_2-O-CH_2CH_2-O-C_4H_9$ | |
| 5 | 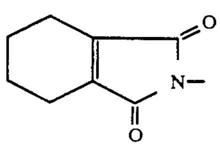 | Cl | $-CH_2CH_2-O-CH_2CH_2-O-C_4H_9$ | |
| 6 | 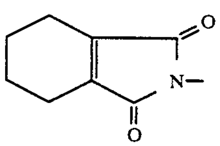 | Cl | $-CH_2CH_2-O-CH_2CH_2-O-CH_3$ | |
| 7 | 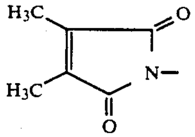 | Cl | $-CH_2CH_2-O-CH_2-CH_2-O-CH_3$ | |
| 8 | 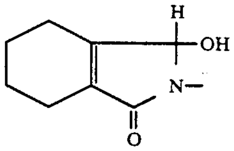 | Cl | $-CH_2CH_2-O-CH_2CH_2-O-C_2H_5$ | |
| 9 | 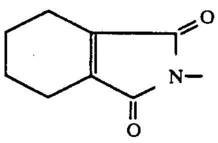 | Cl | 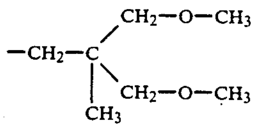 | 75 |
| 10 | 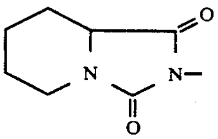 | Cl | 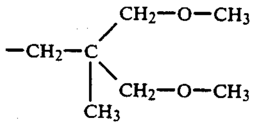 | 78 |
| 11 | 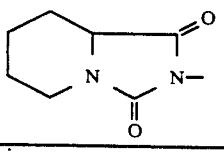 | Cl | $-CH_2CH_2-O-CH_2CH_2-O-CH_3$ | Oil |

Starting substances of the formula (III)

Example (III-1)

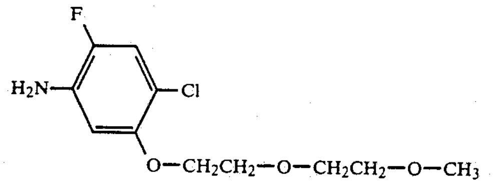

20 g (0.124 mol) of 4-chloro-2-fluoro-5-hydroxyaniline are dissolved in 140 ml of N-methylpyrrolidone, and 10.2 g (0.186 mol) of potassium hydroxide in 12 ml of water and also 35.6 g (0.130 mol) of 2-(2-methoxy-ethoxy)-ethyl p-toluenesulphonate are added in succession. The mixture is stirred at room temperature for 18 hours, and most of the solvent is then removed in vacuo. 200 ml of water are added to the oily residue, and the oil which separates is extracted using dichloromethane. The organic phase is separated off, washed, dried and concentrated in vacuo.

As the residue, 30.5 g (93.3 % of theory) of 4-chloro-2-fluoro-5-[2-(2-methoxy-ethoxy)-ethoxy]-aniline remain as an oil.

$^1$H-NMR ($CDCl_3$): $\delta=6.98$ ppm (1H, d).

Example (III-2)

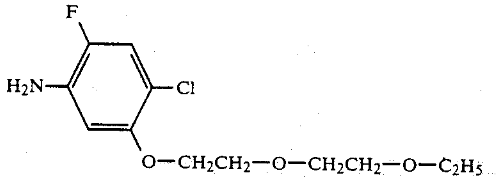

5.5 g (0.018 mol) of 2-chloro-4-fluoro-5-nitro-[2-(2-ethoxy-ethoxy)-ethyl]-phenol are dissolved in 100 ml of ethanol, 1.0 g of 5% platinum on active charcoal are added, and the mixture is hydrogenated at 40° C. using hydrogen under atmospheric pressure. When the reaction is complete, the catalyst is filtered off and the solvent is removed in vacuo.

4.5 g (90.7 % of theory) of 4-chloro-2-fluoro-5 -[2-(2-ethoxy-ethoxy)-ethoxy]-aniline are obtained as an oil.

$^1$H-NMR ($CDCl_3$): $\delta=7.00$ ppm (1H, d).

Starting substances of the formula (XI)

Example (XI-1)

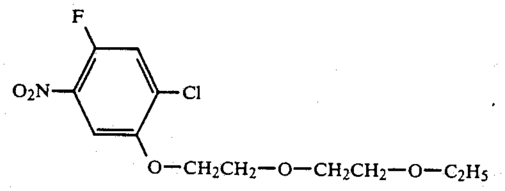

5 g (0.026 mol) of 2-chloro-4-fluoro-5-nitrophenol are dissolved in 10 ml of dimethyl sulphoxide and 0.8 g (0.0267 mol) of sodium hydride (80 % strength) and 7.7 g (0.0267 mol) of 2-(2-ethoxy-ethoxy)-ethyl p-toluene-sulphonate are added in succession. The mixture is heated at 80° C. for 8 hours, then poured out into water, and the precipitated oil is extracted using dichloromethane. The organic phase is washed, dried and concentrated.

5.9 g (72 % of theory) of 4-chloro-2-fluoro-5-[2-(2-ethoxy-ethoxy)-ethoxy]-nitrobenzene are obtained.

$^1$H-NMR ($CDCl_3$): $\delta=7.70$ ppm (1H, d).

Use Examples

In the following Use Examples, the compound listed below is used as comparison substance:

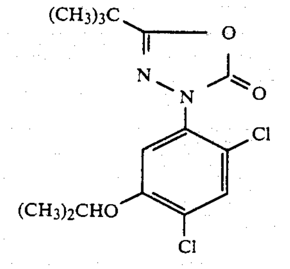

(A)

5-tert-tutyl-3-(2,4-dichloro-5-isopropoxy-phenyl)-1,3,4-oxadiazol-2-one (oxadizone/ ®Ronstar)—disclosed in U.S. Pat. No. 3,835,862.

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

In this test, for example the compound of Preparation Example (1) has a clearly superior activity compared with the known compound (A).

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in damage in comparison to the development of the untreated control. The figures denote:

0% = no action (like untreated control)

100% = total destruction

In this test, for example the compound of Preparation Example (1) has a clearly superior activity compared with the known compound (A).

Example C

Defoliation and desiccation of the leaves of cotton

Solvent: 30 parts by weight of dimethylformamide

Emulsifier: 1 part by weight of polyoxyethylene sorbitan monolaurate

To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

In this test, for example, the compound of Preparation Example (1) shows a clear superiority compared with the untreated control.

It will be understood that the specification and examples are illustrative but not limitative of the present invention and that other embodiments within the spirit and scope of the invention will suggest themselves to those skilled in the art.

We claim:

1. A substituted N-aryl nitrogen heterocycle of the formula

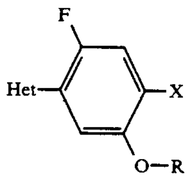

(I)

in which

Het stands for

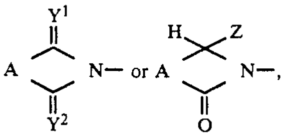

where

A stands for

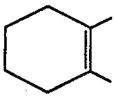 , 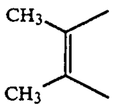 or 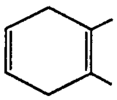 , $Y^1$ and $Y^2$ in each case stands for oxygen or sulphur, Z stands for hydrogen, hydroxyl or chlorine, R stands for alkyl or alkenyl having 2 to 20 carbon atoms, in each case optionally branched, and in each case interrupted by at least one oxygen atom, and X stands for hydrogen or halogen.

2. A compound according to claim 1, in which

R stands for alkyl or alkenyl, in each case having 2 to 20 carbon atoms, in each case optionally branched; and in each case interrupted by 1 to 4 oxygen atoms, and X stands for hydrogen, fluorine, chlorine or bromine.

3. A compound according to claim 1, in which $R^1$ and $R^2$ in each case independently of one another stand for hydrogen, methyl or trifluoromethyl, R stands for alkyl or alkenyl, in each case having 2 to 8 carbon atoms, in each case optionally branched, and in each case interrupted by 1 to 4 oxygen atoms, and X stands for hydrogen, chlorine or bromine.

4. A compound according to claim 1, wherein such compound is N-(4-chloro-2-fluoro-5-[2-(2-ethoxy-ethoxy)-ethoxy]-phenyl-3,4,5,6-tetrahydrophthalimide of the formula

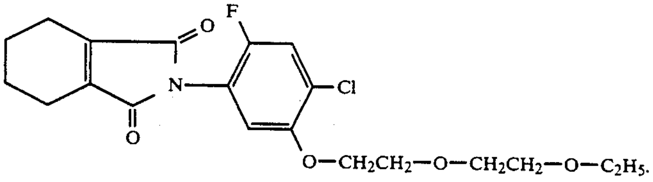

5. A compound according to claim 1, wherein such compound is N-[4-chloro-2-fluoro-5-[2-(2-ethoxy-ethoxy)-ethoxy]-phenyl]-2,3-dimethylmaleimide of the formula

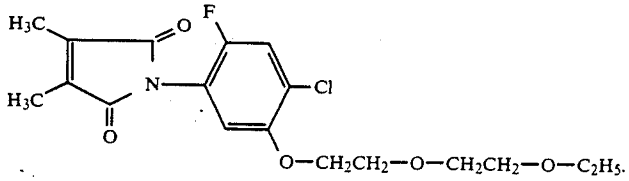

6. A compound according to claim 1, wherein such compound is N-[4-chloro-2-fluoro-5-[2-(2-butoxy-ethoxy)-ethoxy]-phenyl]-2,3-dimethylmaleimide of the formula

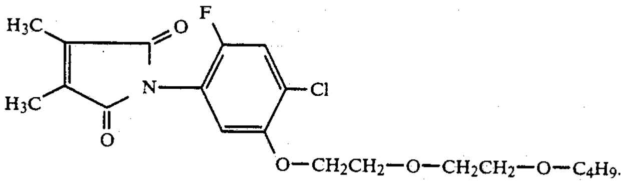

7. A compound according to claim 1, wherein such compound is N-[4-chloro-2-fluoro-5-2-(2-butoxy-ethoxy)-ethoxy]-phenyl]-3,4,5,6-tetrahydrophthalimide of the formula

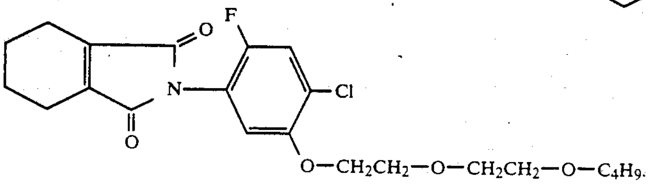

8. A compound according to claim 1, wherein such compound is N-[4-chloro-2-fluoro-5-[2-(2-methoxy-ethoxy)-ethoxy]-phenyl]-3,4,5,6-tetrahydrophthalimide of the formula

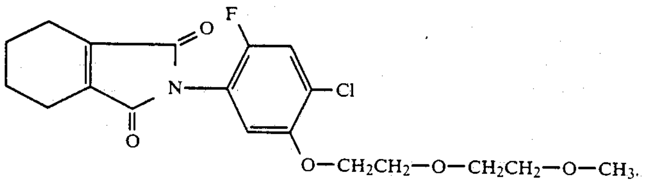

9. A compound according to claim 1, wherein such compound is N-[4-chloro-2-fluoro-5-[2-(2-methoxy-ethoxy)-ethoxy]-phenyl]-2,3-dimethylmaleimide of the formula

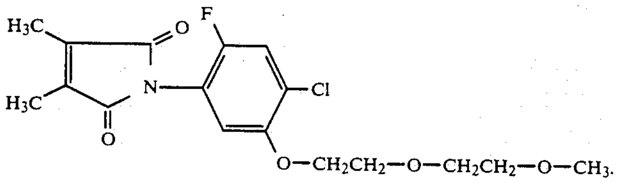

10. A compound according to claim 1, wherein such compound is N-[2-fluoro-4-chloro-5-[2-(2-ethoxy-ethoxy)-ethoxy]-phenyl)-3-hydroxy-2,3,4,5,6,7-hexahydro-isoindole-1(1H)-on the formula

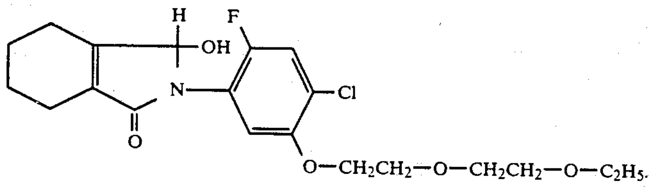

11. A compound according to claim 1, wherein such compound is N-[4-chloro-2-fluoro-5-[3-(2,2-bis-methoxymethyl)-propoxy]-phenyl]-3,4,5,6-tetrahydrophthalimide of the formula

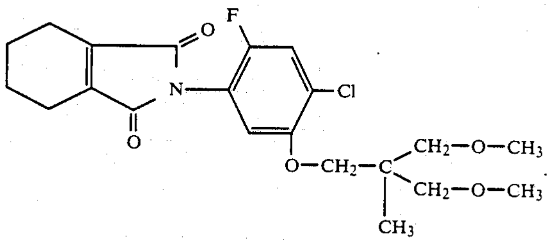

12. A herbicidal composition comprising a herbicidally effective amount of a compound according to claim 1 and a diluent.

13. A method of combating unwanted vegetation which comprises applying to such vegetation or to a locus from which it is desired to exclude such vegetation a herbicidally effective amount of a compound according to claim 1.

14. The method according to claim 13, wherein such compound is

N-(4-chloro-2-fluoro-5-[2-(2-ethoxy-ethoxy)-ethoxy-phenyl)-3,4,5,6-tetrahydrophthalimide, N-(4-chloro-2-fluoro-5-[2-(2-ethoxy-ethoxy)-ethoxyl]-phenyl]-2,3-dimethylmaleimide, N-(4-chloro-2-fluoro-5-[2-(2-butoxy-ethoxy)-ethoxy]-phenyl]-2,3-dimethylmaleimide, N-(4-chloro-2-fluoro-5-[2-(2-butoxy-ethoxy)-ethoxy]-phenyl]-3,4,5,6-tetrahydrophthalimide, N-(4-chloro-2-fluoro-5-[2-(2-butoxy-ethoxy)-ethoxy]-phenyl]-3,4,5,6-tetrahydrophthalimide, N-(4-chloro-2-fluoro-5-[2-(2-butoxy-ethoxy)-ethoxy]-phenyl]-2,3-dimethylmaleimide, N-(2-fluoro-2-chloro-5-[2-(2-butoxy-ethoxy)-ethoxy]-phenyl]-3-hydroxy-2,3,4,5,6,7-hexahydro-isoindole-1(1H)-on, or N-(4-chloro-2-fluoro-5-[3-(2,2-bis-methoxymethyl)-propoxy]-phenyl]-3,4,5,6-tetrahydrophthalimide.

15. A plant growth-regulating composition comprising a plant growth-regulating effective amount of a compound according to claim 1 and a diluent.

16. A method of regulating the growth of a plant which comprises applying to such plant or to a locus in which such plant is growing or is to be grown a plant growth-regulating effective amount of a compound according to claim 1.

17. The method according to claim 16, wherein such compound is N-(4-chloro-2-fluoro-5-[2-(2-ethoxy-ethoxy)-ethoxy]-phenyl)-3,4,5,6-tetrahydrophthalimide.

* * * * *

UNITED STATES PATENT AND TRADEMARK OFFICE

CERTIFICATE OF CORRECTION

PATENT NO. : 5,039,334

DATED : August 13, 1991

INVENTOR(S) : Schallner et al.

It is certified that error appears in the above-identified patent and that said Letters Patent is hereby corrected as shown below:

| | |
|---|---|
| Col. 107, line 11 | After " 5- " insert -- [ -- |
| Col. 108, line 67 | After last " ethoxy " insert -- ] -- |
| Col. 109, lines 1-2 | Delete " ethoxyl] " and substitute -- ethoxy]-- |
| Col. 109, line 7 | Delete " butoxy " and substitute -- methoxy -- |
| Col. 109, line 10 | Delete " butoxy " and substitute -- methoxy -- |
| col. 109, line 12 | Delete " butoxy " and substitute -- ethoxy -- |

Signed and Sealed this

Twenty-fifth Day of May, 1993

Attest:

Michael K. Kirk

MICHAEL K. KIRK

*Attesting Officer*

*Acting Commissioner of Patents and Trademarks*